United States Patent
Butlin

(10) Patent No.: US 6,369,273 B1
(45) Date of Patent: Apr. 9, 2002

(54) CHEMICAL COMPOUNDS AND THEIR USE TO ELEVATE PYRUVATE DEHYDROGENASE ACTIVITY

(75) Inventor: Roger J Butlin, Macclesfield (GB)

(73) Assignee: AstraZeneca AB, Södertaälje (SE)

( * ) Notice: Subject to any disclaimer, the term of this patent is extended or adjusted under 35 U.S.C. 154(b) by 0 days.

(21) Appl. No.: 09/601,449

(22) PCT Filed: Mar. 2, 1999

(86) PCT No.: PCT/GB99/00615

§ 371 Date: Aug. 2, 2000

§ 102(e) Date: Aug. 2, 2000

(87) PCT Pub. No.: WO99/44618

PCT Pub. Date: Sep. 10, 1999

(30) Foreign Application Priority Data

Mar. 6, 1998 (GB) .............................................. 9804648

(51) Int. Cl.$^7$ ........................ C07C 233/05; A61K 31/16

(52) U.S. Cl. ........................ 564/202; 514/269; 514/274; 514/347; 514/369; 514/398; 514/445; 514/473; 514/522; 514/628; 544/301; 546/294; 548/186; 548/187; 548/323.5; 549/65; 549/479; 558/413; 558/414; 558/415; 558/418; 564/138

(58) Field of Search ................................. 514/628, 347, 514/269, 274, 369, 398, 522, 473, 445; 564/202, 138; 558/413, 414, 415, 418; 546/294; 548/186, 187, 323.5; 549/65, 479; 544/301

(56) References Cited

U.S. PATENT DOCUMENTS

| 4,537,618 A | 8/1985 | Schurter et al. ............. 544/321 |
| 5,248,693 A | 9/1993 | Gerspacher et al. ........ 548/511 |
| 5,486,515 A | 1/1996 | Brown et al. |
| 5,510,386 A | 4/1996 | Empfield et al. ............. 546/89 |

FOREIGN PATENT DOCUMENTS

| CA | 1 228 355 | 10/1987 |
| EP | 0 002 309 | 6/1979 |
| EP | 0 002 892 | 7/1979 |
| EP | 0 040 932 | 12/1981 |
| EP | 0 079 191 | 5/1983 |
| EP | 0 096 002 | 12/1983 |
| EP | 0 100 172 | 2/1984 |
| EP | 0 253 500 | 1/1988 |
| EP | 0 253 503 | 1/1988 |
| EP | 0 524 781 | 1/1993 |
| EP | 0 617 010 | 9/1994 |
| EP | 0 625 511 | 11/1994 |
| EP | 0 625 516 | 11/1994 |
| GB | 2 278 054 | 11/1994 |
| WO | WO 93/10094 | 5/1993 |
| WO | WO 93/23358 | 5/1993 |
| WO | WO 94/26739 | 11/1994 |
| WO | WO 96/28151 | 9/1996 |
| WO | WO 97/38124 | 10/1997 |
| WO | WO 99/44618 | 9/1999 |
| WO | WO 99/47508 | 9/1999 |
| WO | WO 99/62506 | 12/1999 |
| WO | WO 99/62873 | 12/1999 |

OTHER PUBLICATIONS

Fenwick, Tertahedron Lett., vol. 34, No. 11, pp 1815–1818, 1993.*

Ohnmacht et al, J. Med. Chem., vol. 39, pp 4592–4601.*

Bayles et al., "A Smiles Rearrangement Involving Non–Activated Aromatic Systems; the Facile Conversion of Phenols to Anilines", Synthesis, 1977, vol. 1. pp. 33–34.

Bayles et al.,, "The Smiles Rearrangement of 2–Aryloxy–2–methylpropanamides. Synthesis of N–Aryl–2–hydroxy–2–methyl–propanamides", Synthesis, 1977, vol. 1, pp, 31–33.

Empfield et al., "4–sulfonamidoanilide Tertiary Carbinols: A Novel Series Of Potassium Cahnnel Openers", Bioorg Med. Chem. Letters, 1997, vol. 7, No. 7, pp. 775–778, XP004136128 see table I, compounds e, f.

Furr et al., "A Novel Non–Steroidal, Peripherally Selective Antiandrogen", J. Endrocrinol., 1987, vol. 113 (3), R7–R9.

Glen et al., Structure–Activity Relationships among Non–steriodal Antiandrogens, Third SCI–RSC Medicinal Chemistry Symposium, 1986, vol. 55, pp. 345–361.

Grant et al., "Anilide Tertiary Carbinols: A New Structural Calss Of Potent Potassium Channel Openers", Bioorg. Med. Chem. Lett., 1993, vol. 3 (12), pp. 2723–2724.

Howe et al., "ZENECA ZD6169: A Novel $K_{ATP}$ Channel Opener with in Vivo Selectivity for Urinary Bladder", J. Pharmacol. Exp. Ther. 1995, vol. 274 (2), pp. 884–890.

(List continued on next page.)

Primary Examiner—Shailendra Kumar
(74) Attorney, Agent, or Firm—Pillsbury Winthrop LLP

(57) ABSTRACT

The use of a compound of the formula (I):

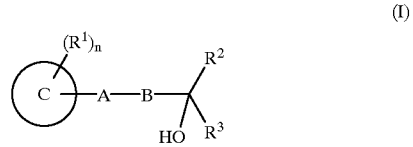

wherein: ring C is phenyl or carbon-linked heteroaryl selected from pyridyl, pyrazinyl, pyrimidinyl and pyridazinyl; and wherein said phenyl or heteroaryl is substituted as defined herein; A—B is selected from NHCO, OCH$_2$, SCH$_2$, NHCH$_2$, trans-vinylene, and ethynylene; R$^1$ is linked to ring C at a carbon ortho to the position of A—B attachment and is defined herein; n is 1 or 2; R$^2$ and R$^3$ are alkyl, haloalkyl or together from cycloalkyl or halocycloalkyl as defined herein; in the manufacture of a medicament for use in the elevation of PDH activity in warm-blooded animals such as humans is described. Salts and esters of compounds of formula (I) are also described.

10 Claims, No Drawings

OTHER PUBLICATIONS

Jackman et al., "Studies in the Field of Diuretics", J. Pharm. and Pharmacol., vol. 12, 1960, pp. 648–655; Chemical Abstracts, vol. 55, No. 9, May 1, 1961, Columbus Ohio, US; abstract No. 8336a, XP002107578 see abstract, col. 8336, lines 8–9 &.

Li et al., "Zeneca ZD6169 and Its Analogs from a Novel Series of Anilide Tertiary Carbinols: in vitro $K_{ATP}$ Channel Opening Acitivity in bladder Detrusor", Pharmacology, 1995, vol. 51, pp. 33–42.

Morris et al., "Hydrogen Bonding Parameters In The S.A.R. of Non–Steroidal Anti–Androgens", Pharmacol. Libr., 1987, vol. 10, pp. 204–206.

Morris et al., "Non–Steroidal Antiandrogens. Design of Novel Compounds Based on an Infrared Study of the Dominant Conformationand Hydrogen–Bonding Properties of a Series of Anilide Antiandrogens", J. Med. Chem. 1991, vol. 34, pp. 447–445.

Ohnmacht et al., N–Aryl–3,3,3–trifluoro–2–hydroxy–2–methylpropanamides: $K_{ATP}$ Potassium Channel Openers. Modifications on the Western Region, J. Med. Chem., 1996, vol. 39 (23), pp. 4592–4601.

Ohnmacht et al., N–Aryl–3,3,3–trifluoro–2–hydroxy–2–methylpropanamides: $K_{ATP}$ Potassium Channel Openers. Modifications on the Western Region, J. Med. Chem., 1996, Additions and Corrections, vol. 40 (6), p. 1048.

Russell, "Crystal Receptor Models In Medicinal Chemistry: Application To The Generation of Highly Potent Potassium Channel Openers", Bioorg. Med. Chem. Lett. 1996, vol. 6 (7), pp. 913–918.

Tenthorey et al.; "New Antiarrhythmic Agents. 3. Primary β–Amino Anilides", J. Med. Chem. 1979, vol. 22 (10), pp. 1182–1186.

Trivedi et al., "K–Channel Opening Acitivity of ZD6169 and Its Analogs: Effect on $^{86}$Rb Efflux and $^{3}$H–1075 Binding in Bladder Smooth Muscle", Pharmacology, 1995, vol. 50 (6), pp. 388–397.

Tucker et al., "Nonsteroidal Antiandrogens. Synthesis and Structure–Activity Relationships of 3–Substituted Derivatives of 2–Hydroxypropionanilides", J. Med. Chem., 1988, vol. 31, pp. 954–959.

Tucker et al., "Resolution of the Nonsteriodal Antiandrogen 4'–Cyano–3–[(4–fluorophenyl)sulfonyl]–2–hydroxy–2–methyl–3'–(trifluoromethyl)–propionanilide and the Determination of the Absolute Configuration of the Active Enantiomer", J. Med. Chem. 1988. vol. 31 (4), pp. 885–887.

Wakeling et al., "Receptor Binding And Biological Activity Of Sterdiodal and Nonsteriodal Antiandrogens", J. Steriod Biochem., 1981, vol. 15, pp. 355–359.

* cited by examiner

CHEMICAL COMPOUNDS AND THEIR USE TO ELEVATE PYRUVATE DEHYDROGENASE ACTIVITY

This application is the national phase of international application PCT/GB99/00615 filed Mar. 2, 1999 which designated the U.S.

The present invention relates to compounds which elevate pyruvate dehydrogenase (PDH) activity, processes for their preparation, pharmaceutical compositions containing them as active ingredient, methods for the treatment of disease states associated with reduced PDH activity, to their use as medicaments and to their use in the manufacture of medicaments for use in the elevation of PDH activity in warm-blooded animals such as humans.

Within tissues adenosine triphosphate (ATP) provides the energy for synthesis of complex molecules and, in muscle, for contraction. ATP is generated from the breakdown of energy-rich substrates such as glucose or long chain free fatty acids. In oxidative tissues such as muscle the majority of the ATP is generated from acetyl CoA which enters the citric acid cycle, thus the supply of acetyl CoA is a critical determinant of ATP production in oxidative tissues. Acetyl CoA is produced either by β-oxidation of fatty acids or as a result of glucose metabolism by the glycolytic pathway. The key regulatory enzyme in controlling the rate of acetyl CoA formation from glucose is PDH which catalyses the oxidation of pyruvate to acetyl CoA and carbon dioxide with concomitant reduction of nicotinamide adenine dinucleotide (NAD) to NADH.

In disease states such as both non-insulin dependent (NIDDM) and insulin-dependent diabetes mellitus (IDDM), oxidation of lipids is increased with a concomitant reduction in utilisation of glucose, which contributes to the hyperglycaemia. Reduced glucose utilisation in both IDDM and NIDDM is associated with a reduction in PDH activity. In addition, a further consequence of reduced PDH activity may be that an increase in pyruvate concentration results in increased availability of lactate as a substrate for hepatic gluconeogenesis. It is reasonable to expect that increasing the activity of PDH could increase the rate of glucose oxidation and hence overall glucose utilisation, in addition to reducing hepatic glucose output. Another factor contributing to diabetes mellitus is impaired insulin secretion, which has been shown to be associated with reduced PDH activity in pancreatic β-cells (in a rodent genetic model of diabetes mellitus Zhou et al. (1996) Diabetes 45: 580–586).

Oxidation of glucose is capable of yielding more molecules of ATP per mole of oxygen than is oxidation of fatty acids. In conditions where energy demand may exceed energy supply, such as myocardial ischaemia, intermittent claudication, cerebral ischaemia and reperfusion, (Zaidan et al., 1998; J. Neurochem. 70: 233–241), shifting the balance of substrate utilisation in favour of glucose metabolism by elevating PDH activity may be expected to improve the ability to maintain ATP levels and hence function.

An agent which is capable of elevating PDH activity may also be expected to be of benefit in treating conditions where an excess of circulating lactic acid is manifest such as in certain cases of sepsis.

The agent dichloroacetic acid (DCA) which increases the activity of PDH after acute administration in animals, (Vary et al., 1988; Circ. Shock, 24: 3–18), has been shown to have the predicted effects in reducing glycaemia, (Stacpoole et al., 1978; N. Engl. J. Med. 298: 526–530), and as a therapy for myocardial ischaemia (Bersin and Stacpoole 1997; American Heart Journal, 134: 841–855) and lactic acidaemia, (Stacpoole et al., 1983; N. Engl. J. Med. 309: 390–396).

PDH is an intramitochondrial multienzyme complex consisting of multiple copies of several subunits including three enzyme activities E1, E2 and E3, required for the completion of the conversion of pyruvate to acetyl CoA (Patel and Roche 1990; FASEB J., 4: 3224–3233). E1catalyses the non-reversible removal of $CO_2$ from pyruvate; E2 forms acetyl CoA and E3 reduces NAD to NADH. Two additional enzyme activities are associated with the complex: a specific kinase which is capable of phosphorylating E1 at three serine residues and a loosely-associated specific phosphatase which reverses the phosphorylation. Phosphorylation of a single one of the three serine residues renders the E1 inactive. The proportion of the PDH in its active (dephosphorylated) state is determined by a balance between the activity of the kinase and phosphatase. The activity of the kinase may be regulated in vivo by the relative concentrations of metabolic substrates such as NAD/NADH, CoA/acetylCoA and adenine diphosphate (ADP)/ATP as well as by the availability of pyruvate itself.

European Patent Publication No. 617010 describes compounds which are capable of relaxing bladder smooth muscle and which may be used in the treatment of urge incontinence. Whilst the compounds of the present invention fall within the general structural disclosure of EP 0617010, we have found, surprisingly, that the compounds of the present invention are very good at elevating PDH activity, a property nowhere disclosed in EP 0617010.

The present invention is based on the surprising discovery that certain compounds elevate PDH activity, a property of value in the treatment of disease states associated with disorders of glucose utilisation such as diabetes mellitus, obesity, (Curto et al., 1997; Int. J. Obes. 21: 1137–1142), and lactic acidaemia. Additionally the compounds may be expected to have utility in diseases where supply of energy-rich substrates to tissues is limiting such as peripheral vascular disease, (including intermittent claudication), cardiac failure and certain cardiac myopathies, muscle weakness, hyperlipidaemias and atherosclerosis (Stacpoole et al., 1978; N. Engl. J. Med. 298: 526–530). A compound that activates PDH may also be useful in treating Alzheimer disease (AD) (J Neural Transm (1998) 105: 855–870).

According to one aspect of the present invention there is provided the use of a compound of the formula (I):

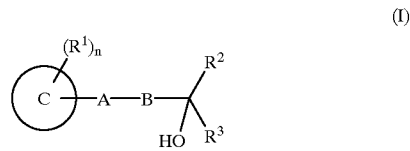

(I)

wherein:
ring C is phenyl or carbon-linked heteroaryl selected from pyridyl, pyrazinyl, pyrimidinyl and pyridazinyl; wherein said phenyl or heteroaryl is substituted on carbon at one or both positions meta to the position of A—B attachment or on carbon at the position para to the position of A—B attachment by a group selected from cyano, trifluoromethyl, nitro, trifluoromethoxy, trifluoromethylthio and a group ArY; and further, wherein said phenyl or heteroaryl is substituted on carbon at any remaining meta position(s) or para position by a group or groups independently selected from hydrogen, (1–4C)alkyl, (1–4C)haloalkyl, (1–4C) alkoxy, (1–4C)haloalkoxy, (1–4C)alkenyloxy, cyano, nitro, halo, hydroxy and trifluoromethylthio; in which Ar is selected from the group consisting of phenyl, a carbon-linked six-membered heteroaryl ring containing 1–2 nitrogen atoms and a carbon-linked five-membered heteroaryl ring containing from 1–2 heteroatoms selected from nitrogen, oxygen, and sulphur; wherein said phenyl or heteroaryl ring Ar is optionally substituted at carbon, with 1–4 substituents selected from (1–4C)alkyl, (1–4C)haloalkyl, (1–4C)alkoxy, (1–4C)haloalkoxy, (2–4C)alkenyloxy, cyano, nitro, halo and trifluoromethylthio;

Y is selected from carbonyl, sulphinyl and sulphonyl;

A—B is selected from NHCO, OCH$_2$, SCH$_2$, NHCH$_2$, trans-vinylene, and ethynylene;

R$^1$ is linked to ring C at a carbon ortho to the position of A—B attachment and is selected from the group consisting of (1–4C)alkyl, (1–4C)haloalkyl, (1–4C)alkoxy, (1–4C)haloalkoxy, (2–4C)alkenyloxy, cyano, nitro, halo, trifluoromethylthio and hydroxy;

n is 1 or 2;

R$^2$ and R$^3$ are independently (1–3C)alkyl optionally substituted by from 1 to 2k+1 atoms selected from fluoro and chloro wherein k is the number of carbon atoms in the said (1–3C)alkyl, provided that R$^2$ and R$^3$ are not both methyl; or R$^2$ and R$^3$, together with the carbon atom to which they are attached, form a 3–5 membered cycloalkyl ring optionally substituted by from 1 to 2 m–2 fluorine atoms wherein m is the number of carbon atoms in said ring;

and a pharmaceutically acceptable in vivo cleavable ester of said compound of formula (I);

and a pharmaceutically acceptable salt of said compound or said ester;

provided said compound is not
N-(4-benzoyl-2,6-dimethylphenyl)-2-hydroxy-2-methyl-3,3,3-trifluoropropanamide, in the manufacture of a medicament for use in the elevation of PDH activity in warm-blooded animals such as humans.

Preferably ring C is phenyl or carbon-linked pyridyl wherein said phenyl or pyridyl is substituted as defined hereinbefore.

More preferably ring C is phenyl or carbon-linked pyridyl wherein said phenyl or pyridyl is substituted on carbon at the position para to the position of A—B attachment by a group selected from cyano, trifluoromethyl, nitro, trifluoromethoxy, trifluoromethylthio and a group ArY (wherein A—B and ArY are as defined hereinbefore).

Particularly ring C is phenyl or carbon-linked pyridyl wherein said phenyl or pyridyl is substituted on carbon at the position para to the position of A—B attachment by a group selected from cyano, trifluoromethyl, nitro, trifluoromethoxy and a group ArY (wherein A—B and ArY are as defined hereinbefore).

More particularly ring C is phenyl or carbon-linked pyridyl wherein said phenyl or pyridyl is substituted on carbon at the position para to the position of A—B attachment by a group selected from cyano, trifluoromethyl, nitro and a group ArY (wherein A—B and ArY are as defined hereinbefore).

Particularly preferred ring C is phenyl or carbon-linked pyridyl wherein said phenyl or pyridyl is substituted on carbon at the position para to the position of A—B attachment by a group ArY (wherein A—B and ArY are as defined hereinbefore).

Especially ring C is phenyl and is substituted as defined hereinbefore.

More especially ring C is phenyl wherein said phenyl is substituted on carbon at the position para to the position of A—B attachment by a group selected from cyano, trifluoromethyl, nitro, trifluoromethoxy and a group ArY (wherein A—B and ArY are as defined hereinbefore).

Particularly preferred ring C is phenyl wherein said phenyl is substituted on carbon at the position para to the position of A—B attachment by a group ArY (wherein A—B and ArY are as defined hereinbefore).

More especially ring C is phenyl which is substituted on carbon at the position para to the position of A—B attachment by a group ArY (wherein A—B and ArY are as defined hereinbefore).

In one embodiment of the present invention Ar is phenyl, 4-pyridyl, 2-thienyl, 2-pyrimidyl, 2-imidazolyl, 2-pyridyl, 3-pyridyl, 2-thiazolyl or 3-furyl and is optionally substituted as defined hereinbefore.

In a further embodiment of the present invention Ar is phenyl (optionally substituted with fluoro, methoxy, bromo, trifluoromethyl, nitro or methyl), or Ar is 4-pyridyl, 5-methylthien-2-yl, 2-pyrimidyl, 2-imidazolyl, 2-pyridyl, 3-pyridyl, 2-thiazolyl or 2-methylfur-3-yl.

In another embodiment of the present invention Ar is phenyl or 4-pyridyl and is optionally substituted as defined hereinbefore.

In an alternative embodiment of the present invention Ar is phenyl and is optionally substituted as defined hereinbefore.

In an additional aspect of the invention Ar is selected from the group consisting of a carbon-linked six-membered heteroaryl ring containing 1–2 nitrogen atoms and a carbon-linked five-membered heteroaryl ring containing from 1–2 heteroatoms selected from nitrogen, oxygen, and sulphur; wherein said heteroaryl ring (Ar) is optionally substituted as defined hereinbefore.

In one aspect of the invention, preferably Y is sulphinyl or sulphonyl.

Preferably A—B is NHCO or ethynylene.

More preferably A—B is NHCO.

Preferably R$^1$ is selected from the group consisting of (1–4C)alkyl, (1–4C)haloalkyl, (1–4C)alkoxy, cyano, nitro, halo and hydroxy.

More preferably R$^1$ is selected from the group consisting of (1–2C)alkyl, (1–2C)alkoxy, cyano, nitro, halo and hydroxy.

Particularly R$^1$ is selected from methyl, methoxy, nitro, fluoro, chloro, bromo and hydroxy.

More particularly R$^1$ is selected from methoxy, nitro, fluoro, chloro, bromo and hydroxy.

Especially R$^1$ is fluoro, chloro or bromo.

Preferably n is 1.

Preferably R$^2$ and R$^3$ are independently (1–3C)alkyl optionally substituted by from 1 to 2k+1 atoms selected from fluoro and chloro, wherein k is the number of carbon atoms in the said (1–3C)alkyl, provided that R$^2$ and R$^3$ are not both methyl; or R$^2$ and R$^3$, together with the carbon atom to which they are attached, form a cyclopropane ring optionally substituted by from 1 to 4 fluorine atoms.

More preferably R$^2$ and R$^3$ are independently (1–2C)alkyl optionally substituted by from 1 to 2k+1 fluorine atoms, wherein k is the number of carbon atoms in the said (1–2C)alkyl, provided that R$^2$ and R$^3$ are not both methyl; or R$^2$ and R$^3$, together with the carbon atom to which they are attached, form a Cyclopropane ring optionally substituted by from 1 to 4 fluorine atoms.

Particularly R$^2$ and R$^3$ are independently methyl, fluoromethyl, difluoromethyl, Trifluoromethyl, 2,2,2- trifluoroethyl and perfluoroethyl provided that $R^2$ and $R^3$ are not both methyl; or $R^2$ and $R^3$, together with the carbon atom to which they are attached, form a cyclopropane ring optionally substituted by from 1 to 4 fluorine atoms.

More particularly $R^2$ and $R^3$ are independently methyl, fluoromethyl, difluoromethyl and trifluoromethyl, provided that $R^2$ and $R^3$ are not both methyl; or $R^2$ and $R^3$, together with the carbon atom to which they are attached, form a cyclopropane ring optionally substituted by from 1 to 4 fluorine atoms.

In another aspect of the invention preferably $R^2$ and $R^3$ are independently methyl, ethyl, difluoromethyl, trifluoromethyl provided that $R^2$ and $R^3$ are not both methyl; or $R^2$ and $R^3$, together with the carbon atom to which they are attached, form a cyclopropane ring.

In a further aspect of the invention preferably one of $R^2$ and $R^3$ is methyl and the other is trifluoromethyl.

Where applicable, the R-configuration at the carbinol centre generally represents a preferred stereochemistry for compounds of formula (I).

According to another aspect of the present invention there is provided the use of a compound of the formula (Ia):

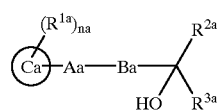

(Ia)

wherein:

ring Ca is phenyl or carbon-linked pyridyl wherein said phenyl or pyridyl is substituted on carbon at the position para to the position of Aa—Ba attachment by a group selected from cyano, trifluoromethyl, nitro, trifluoromethoxy, trifluoromethylthio and a group $ArAY^a$ (wherein Ara is selected from the group consisting of phenyl, a carbon-linked six-membered heteroaryl ring containing 1–2 nitrogen atoms and a carbon-linked five-membered heteroaryl ring containing from 1–2 heteroatoms selected from nitrogen, oxygen, and sulphur; wherein said phenyl or heteroaryl ring Ar is optionally substituted at carbon, with 1–4 substituents selected from (1–4C)alkyl, (1–4C)haloalkyl, (1–4C)alkoxy, (1–4C)haloalkoxy, (2–4C)alkenyloxy, cyano, nitro, halo and trifluoromethylthio, $Y^a$ is selected from carbonyl, sulphinyl and sulphonyl and Aa—Ba is selected from NHCO, $OCH_2$, $SCH_2$, $NHCH_2$, trans-vinylene, and ethynylene);

$R^{1a}$ is linked to ring C at a carbon ortho to the position of Aa—Ba attachment and is selected from the group consisting of (1 4C)alkyl, (1–4C)haloalkyl, (1–4AC)alkoxy, (1–4C)haloalkoxy, (2–4C)alkenyloxy, cyano, nitro, halo, trifluoromethylthio and hydroxy;

na is 1;

$R^{2a}$ and $R^{3a}$ are independently (1–3C)alkyl optionally substituted by from 1 to 2k+1 atoms selected from fluoro and chloro, wherein k is the number of carbon atoms in the said (1–3C)alkyl, provided that $R^{2a}$ and $R^{3a}$ are not both methyl; or $R^{2a}$ and $R^{3a}$, together with the carbon atom to which they are attached, form a cyclopropane ring optionally substituted by from 1 to 4 fluorine atoms;

and a pharmaceutically acceptable in vivo cleavable ester of said compound of formula (Ia);

and a pharmaceutically acceptable salt of said compound or said ester;

in the manufacture of a medicament for use in the elevation of PDH activity in warm-blooded animals such as humans.

Where applicable, the R-configuration generally represents a preferred stereochemistry or compounds of formula (Ia).

According to another aspect of the present invention there is provided the use of a compound of the formula (Ib):

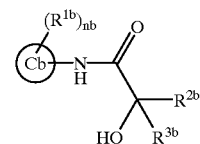

(Ib)

wherein:

ring Cb is phenyl or carbon-linked pyridyl wherein said phenyl or pyridyl is substituted on carbon at the position para to the position of NHCO attachment by a group selected from cyano, trifluoromethyl, nitro, trifluoromethoxy, trifluoromethylthio and a group $ArbY^b$ (wherein Arb is selected from the group consisting of phenyl, a carbon-linked six-membered heteroaryl ring containing 1–2 nitrogen atoms and a carbon-linked five-membered heteroaryl ring containing from 1–2 heteroatoms selected from nitrogen, oxygen, and sulphur; wherein said phenyl or heteroaryl ring Arb is optionally substituted at carbon, with 1–4 substituents selected from (1–4C)alkyl, (1–4C)haloalkyl, (1–4C)alkoxy, (1–4C)haloalkoxy, (2–4C)alkenyloxy, cyano, nitro, halo and trifluoromethylthio and $Y^b$ is selected from carbonyl, sulphinyl and sulphonyl);

$R^{1b}$ is linked at a carbon ortho to the position of NHCO attachment and is selected from the group consisting of (1–4C)alkyl, (1–4C)haloalkyl, (1–4C)alkoxy, (1–4C)haloalkoxy, (2–4C)alkenyloxy, cyano, nitro, halo, trifluoromethylthio and hydroxy;

nb is 1;

$R^{2b}$ and $R^{3b}$ are independently (1–2C)alkyl optionally substituted by from 1 to 2k+1 fluorine atoms, wherein k is the number of carbon atoms in the said (1–2C) alkyl, provided that $R^{2b}$ and $R^{3b}$ are not both methyl; or $R^{2b}$ and $R^{3b}$, together with the carbon atom to which they are attached, form a cyclopropane ring optionally substituted by from 1 to 4 fluorine atoms;

and a pharmaceutically acceptable in vivo cleavable ester of said compound of formula (Ib);

and a pharmaceutically acceptable salt of said compound or said ester;

in the manufacture of a medicament for use in the elevation of PDH activity in warm-blooded animals such as humans.

Where applicable, the R-configuration generally represents a preferred stereochemistry for compounds of formula (Ib).

According to another aspect of the present invention there is provided the use of a compound of the formula (Ic):

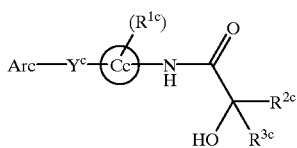

(Ic)

wherein:
  ring Cc is phenyl or carbon-linked pyridyl wherein said phenyl or pyridyl is substituted on carbon at the position para to the position of NHCO attachment by a group ArcY$^c$ (wherein Arc is selected from the group consisting of phenyl, a carbon-linked six-membered heteroaryl ring containing 1–2 nitrogen atoms and a carbon-linked five-membered heteroaryl ring containing from 1–2 heteroatoms selected from nitrogen, oxygen, and sulphur; wherein said phenyl or heteroaryl ring Arc is optionally substituted at carbon, with 1–4 substituents selected from (1–4C)alkyl, (1–4C)haloalkyl, (1–4C)alkoxy, (1–4C)haloalkoxy, (2–4C)alkenyloxy, cyano, nitro, halo and trifluoromethylthio, and Y$^c$ is selected from carbonyl, sulphinyl and sulphonyl);
  R$^{1c}$ is linked at a carbon ortho to the position of NHCO attachment and is selected from the group consisting of (1–2C)alkyl, (1–2C)alkoxy, cyano, nitro, halo and hydroxy;
  R$^{2c}$ and R$^{3c}$ are independently methyl, fluoromethyl, difluoromethyl, trifluoromethyl, 2,2,2-trifluoroethyl, and perfluoroethyl, provided that R$^{2c}$ and R$^{3c}$ are not both methyl; or
  R$^{2c}$ and R$^{3c}$, together with the carbon atom to which they are attached, form a cyclopropane ring optionally substituted by from 1 to 4 fluorine atoms;
and a pharmaceutically acceptable in vivo cleavable ester of said compound of formula (Ic);
and a pharmaceutically acceptable salt of said compound or said ester;
in the manufacture of a medicament for use in the elevation of PDH activity in warm-blooded animals such as humans.

Where applicable, the R-configuration generally represents a preferred stereochemistry for compounds of formula (Ic).

According to another aspect of the present invention there is provided the use of a compound of the formula (Id):

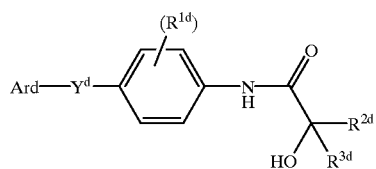

(Id)

wherein:
  Ard is selected from the group consisting of phenyl, a carbon-linked six-membered heteroaryl ring containing 1–2 nitrogen atoms and a carbon-linked five-membered heteroaryl ring containing from 1–2 heteroatoms selected from nitrogen, oxygen, and sulphur; wherein said phenyl or heteroaryl ring Ard is optionally substituted at carbon, with 1–4 substituents selected from (1–4C)alkyl, (1–4C)haloalkyl, (1–4C)alkoxy, (1–4C)haloalkoxy, (2–4C)alkenyloxy, cyano, nitro, halo and trifluoromethylthio and Y$^d$ is selected from carbonyl, sulphinyl and sulphonyl;
  R$^{1d}$ is linked at a carbon ortho to the position of NHCO attachment and is selected from the group consisting of methoxy, nitro, fluoro, chloro, bromo and hydroxy;
  R$^{2d}$ and R$^{3d}$ are independently methyl, fluoromethyl, difluoromethyl, trifluoromethyl, provided that R$^{2d}$ and R$^{3d}$ are not both methyl; or
  R$^{2d}$ and R$^{3d}$, together with the carbon atom to which they are attached, form a cyclopropane ring optionally substituted by from 1 to 4 fluorine atoms
and a pharmaceutically acceptable in vivo cleavable ester of said compound of formula (Id);
and a pharmaceutically acceptable salt of said compound or said ester;
in the manufacture of a medicament for use in the elevation of PDH activity in warm-blooded animals such as humans.

Where applicable, the R-configuration generally represents a preferred stereochemistry for compounds of formula (Id).

Many of the compounds of the present invention are novel and as such are provided as a further feature of the present invention.

According to another aspect of the present invention there is provided a compound of the formula (I):

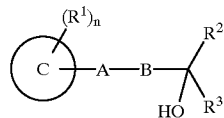

(I)

wherein ring C, R$^1$, n, A—B, R$^2$ and R$^3$ are as defined hereinbefore,
and a pharmaceutically acceptable in vivo cleavable ester of said compound of formula (I);
and a pharmaceutically acceptable salt of said compound or said ester;
provided said compound is not selected from
N-(4-benzoyl-2,6-dimethylphenyl)-2-hydroxy-2-methyl-3,3,3-trifluoropropanamide,
N-(4-benzoyl-2-methylphenyl)-2-hydroxy-2-methyl-3,3,3-trifluoropropanamide,
N-(4-benzoyl-2-fluorophenyl)-2-hydroxy-2-methyl-3,3,3-trifluoropropanamide,
N-(6-chloro-3-phenylsulfonylphenyl)-2-hydroxy-2-methyl-3,3,3-trifluoropropanamide,
2-hydroxy-N-[2-methoxy-4-(4-pyridylsulfonyl)phenyl]-2-methyl-3,3,3-trifluoropropanamide,
2-hydroxy-2-methyl-N-[2-nitro-4-(phenylsulfonyl)phenyl]-3,3,3-trifluoropropanamide,
S-(-)-N-(4-benzoyl-2-methylphenyl)-2-hydroxy-2-methyl-3,3,3-trifluoropropanamide,
N-(4-benzoyl-2-chlorophenyl)-2-hydroxy-2-methyl-3,3,3-trifluoropropanamide,
N-(4-benzoyl-2-bromophenyl)-3,3-difluoro-2-(difluoromethyl)-2-hydroxypropanamide,
N-(4-benzoyl-2-bromophenyl)-2-hydroxy-2-methyl-3,3,3-trifluoropropanamide,
N-(4-benzoyl-2-cyanophenyl)-2-hydroxy-2-methyl-3,3,3-trifluoropropanamide,
N-(4-benzoyl-2-methoxyphenyl)-2-hydroxy-2-methyl-3,3,3-trifluoropropanamide,
N-(4-benzoyl-2-hydroxyphenyl)-2-hydroxy-2-methyl-3,3,3-trifluoropropanamide, 2-hydroxy-N-[2-hydroxy-4(4-pyridylsulfonyl)phenyl]-2-methyl-3,3,3-trifluoropropanamide, N-(4-benzoyl-2,6-dimethylphenyl)-2-hydroxy-2-methyl-3,3,3-trifluoropropanamide, N-(2-Fluoro-5-nitrophenyl)-2-hydroxy-2-trifluoromethylbutanamide, N-(2-Fluoro-5-nitrophenyl)-2-hydroxy-2-difluoromethyl-3,3-difluoropropanamide, and 3-Hydroxy-3-trifluoromethyl-1-(2-chloro-5-trifluoromethylphenyl)-4,4,4-trifluorobut-1-yne, and pharmaceutically acceptable in vivo cleavable esters of said compounds, and pharmaceutically acceptable salts of said compounds and said esters.

According to another aspect of the present invention there is provided a compound of the formula (Ia):

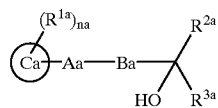

(Ia)

wherein:

ring Ca, $R^{1a}$, na, Aa—Ba, $R^{2a}$ and $R^{3a}$ are as defined hereinbefore, and a pharmaceutically acceptable in vivo cleavable ester of said compound of formula (Ia); and a pharmaceutically acceptable salt of said compound or said ester; provided said compound is not selected from:

N-(4-benzoyl-2-methylphenyl)-2-hydroxy-2-methyl-3,3,3-trifluoropropanamide,

N-(4-benzoyl-2-fluorophenyl)-2-hydroxy-2-methyl-3,3,3-trifluoropropanamide, 2-hydroxy-N-[2-methoxy-4-(4-pyridyl-sulfonyl)phenyl]-2-methyl-3,3,3-trifluoropropanamide, 2-hydroxy-2-methyl-N-[2-nitro-4(phenyl-sulfonyl)phenyl]-3,3,3-trifluoropropanamide, S-(−)-N-(4-benzoyl-2-methylphenyl)-2-hydroxy-2-methyl-3,3,3-trifluoropropanamide, N-(4-benzoyl-2-chlorophenyl)-2-hydroxy-2-methyl-3,3,3-trifluoropropanamide, N-(4-benzoyl-2-bromophenyl)-3,3-difluoro-2-(difluoromethyl)-2-hydroxypropanamide, N-(4-benzoyl-2-bromophenyl)-2-hydroxy-2-methyl-3,3,3-trifluoropropanamide, N-(4-benzoyl-2-cyanophenyl)-2-hydroxy-2-methyl-3,3,3-trifluoropropanamide, N-(4-benzoyl-2-methoxyphenyl)-2-hydroxy-2-methyl-3,3,3-trifluoropropanamide, N-(4-benzoyl-2-hydroxyphenyl)-2-hydroxy-2-methyl-3,3,3-trifluoropropanamide and 2-hydroxy-N-[2-hydroxy-4-(4-pyridylsulfonyl)phenyl]-2-methyl-3,3,3-trifluoropropanamide and pharmaceutically acceptable in vivo cleavable esters of said compounds, and pharmaceutically acceptable salts of said compounds and said esters.

According to another aspect of the present invention there is provided a compound of the formula (Ib):

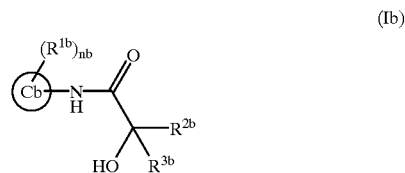

(Ib)

wherein:

Cb, $R^{1b}$, $R^{2b}$, $R^{3b}$ and nb are as defined hereinbefore, and a pharmaceutically acceptable in vivo cleavable ester of said compound of formula (Ib); and a pharmaceutically acceptable salt of said compound or said ester; provided said compound is not selected from:

N-(4-benzoyl-2-methylphenyl)-2-hydroxy-2-methyl-3,3,3-trifluoropropanamide,

N-(4-benzoyl-2-fluorophenyl)-2-hydroxy-2-methyl-3,3,3-trifluoropropanamide, 2-hydroxy-N-[2-methoxy-4-(4-pyridyl-sulfonyl)phenyl]-2-methyl-3,3,3-trifluoropropanamide, 2-hydroxy-2-methyl-N-[2-nitro-4-(phenyl-sulfonyl)phenyl]-3,3,3-trifluoropropanamide, S-(−)-N-(4-benzoyl-2-methylphenyl)-2-hydroxy-2-methyl-3,3,3-trifluoropropanamide, N-(4-benzoyl-2-chlorophenyl)-2-hydroxy-2-methyl-3,3,3-trifluoropropanamide, N-(4benzoyl-2-bromophenyl)-3,3-difluoro-2-(difluoromethyl)-2-hydroxypropanamide, N-(4benzoyl-2-bromophenyl)-2-hydroxy-2-methyl-3,3,3-trifluoropropanamide, N-(4-benzoyl-2-cyanophenyl)-2-hydroxy-2-methyl-3,3,3-trifluoropropanamide, N-(4-benzoyl-2-methoxyphenyl)-2-hydroxy-2-methyl-3,3,3-trifluoropropanamide, N-(4-benzoyl-2-hydroxyphenyl)-2-hydroxy-2-methyl-3,3,3-trifluoropropanamide and 2-hydroxy-N-[2-hydroxy-4(4-pyridylsulfonyl)phenyl]-2-methyl-3,3,3-trifluoropropanamide, and pharmaceutically acceptable in vivo cleavable esters of said compounds, and pharmaceutically acceptable salts of said compounds and said esters.

According to another aspect of the present invention there is provided a compound of the formula (Ic):

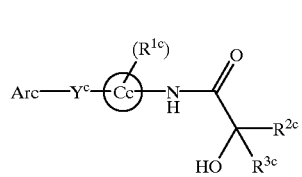

(Ic)

wherein:

Cc, $R^{1c}$, $R^{2c}$, $R^{3c}$, Arc and $Y^c$ are as defined hereinbefore, and a pharmaceutically acceptable in vivo cleavable ester of said compound of formula (Ic); and a pharmaceutically acceptable salt of said compound or said ester; provided said compound is not selected from:

N-(4-benzoyl-2-methylphenyl)-2-hydroxy-2-methyl-3,3,3-trifluoropropanamide,

N-(4-benzoyl1-2-fluorophenyl)-2-hydroxy-2-methyl-3,3,3-trifluoropropanamide, 2-hydroxy-N-[2-methoxy-4-(4-pyridyl-sulfonyl)phenyl]-2-methyl-3,3,3-trifluoropropanamide,
2-hydroxy-2-methyl-N-[2-nitro-4-(phenyl-sulfonyl)phenyl]-3,3,3-trifluoropropanamide,
S-(−)-N-(4-benzoyl-2-methylphenyl)-2-hydroxy-2-methyl-3,3,3-trifluoropropanamide,
N-(4-benzoyl-2-chlorophenyl)-2-hydroxy-2-methyl-3,3,3-trifluoropropanamide,
N-(4-benzoyl-2-bromophenyl)-2-hydroxy-2-methyl-3,3,3-trifluoropropanamide,
N-(4-benzoyl-2-cyanophenyl)-2-hydroxy-2-methyl-3,3,3-trifluoropropanamide,
N-(4-benzoyl-2-methoxyphenyl)-2-hydroxy-2-methyl-3,3,3-trifluoropropanamide,
N-(4-benzoyl-2-hydroxyphenyl)-2-hydroxy-2-methyl-3,3,3-trifluoropropanamide and
2-hydroxy-N-[2-hydroxy-4-(4-pyridylsulfonyl)phenyl]-2-methyl-3,3,3-trifluoropropanamide,
and pharmaceutically acceptable in vivo cleavable esters of said compounds,
and pharmaceutically acceptable salts of said compounds and said esters.

According to another aspect of the present invention there is provided a compound of the formula (Id):

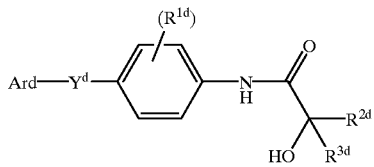

(Id)

wherein:

$R^{1d}$, $R^{2d}$, $R^{3d}$, Ard and $Y^d$ are as defined hereinbefore, and a pharmaceutically acceptable in vivo cleavable ester of said compound of formula (Id);

and a pharmaceutically acceptable salt of said compound or said ester;

provided said compound is not selected from:
N-(4-benzoyl-2-fluorophenyl)-2-hydroxy-2-methyl-3,3,3-trifluoropropanamide,
2-hydroxy-N-[2-methoxy-4-(4-pyridyl-sulfonyl)phenyl]-2-methyl-3,3,3-trifluoropropanamide,
2-hydroxy-2-methyl-N-[2-nitro-4-(phenyl-sulfonyl)phenyl]-3,3,3-trifluoropropanamide,
N-(4-benzoyl-2-chlorophenyl)-2-hydroxy-2-methyl-3,3,3-trifluoropropanamide,
N-(4-benzoyl-2-bromophenyl)-3,3-difluoro-2-(difluoromethyl)-2-hydroxypropanamide,
N-(4-benzoyl-2-bromophenyl)-2-hydroxy-2-methyl-3,3,3-trifluoropropanamide,
N-(4-benzoyl-2-methoxyphenyl)-2-hydroxy-2-methyl-3,3,3-trifluoropropanamide,
N-benzoyl-2-hydroxyphenyl)-2-hydroxy-2-methyl-3,3,3-trifluoropropanamide and
2-hydroxy-N-[2-hydroxy-4-(4-pyridylsulfonyl)phenyl]-2-methyl-3,3,3-trifluoropropanamide,
and pharmaceutically acceptable in vivo cleavable esters of said compounds,
and pharmaceutically acceptable salts of said compounds and said esters.

According to another aspect of the present invention there is provided a compound of the formula (Ie):

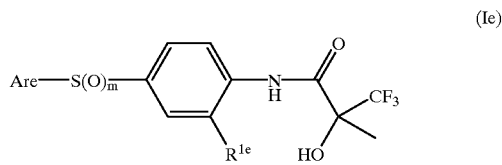

(Ie)

wherein:

$R^{1e}$ is fluoro, chloro or bromo;

m is 1 or 2;

Are is selected from the group consisting of a carbon-linked six-membered heteroaryl ring containing 1–2 nitrogen atoms and a carbon-linked five-membered heteroaryl ring containing from 1–2 heteroatoms selected from nitrogen, oxygen, and sulphur; wherein said heteroaryl ring is optionally substituted at carbon, with 1–4 substituents selected from (1–4C)alkyl, (1–4C)haloalkyl, (1–4C)alkoxy, (1–4C)haloalkoxy, (2–4C)alkenyloxy, cyano, nitro, halo and trifluoromethylthio;

and a pharmaceutically acceptable in vivo cleavable ester of said compound of formula (Ie), and a pharmaceutically acceptable salt of said compound or said ester.

The compounds of the present invention which are of the R-configuration at the carbinol centre form a preferred group of compounds of the present invention. According to another aspect of the present invention there is provided the use of a compound selected from Examples 1, 2, 7, 8 and 10–15 and a pharmaceutically acceptable in vivo cleavable ester of said compound, and a pharmaceutically acceptable salt of said compound or said ester in the manufacture of a medicament for use in the elevation of PDH activity in warm-blooded animals such as humans.

According to a preferred aspect of the present invention there is provided the use of a compound selected from Examples 2 and 10–14 and a pharmaceutically acceptable in vivo cleavable ester of said compound, and a pharmaceutically acceptable salt of said compound or said ester, in the manufacture of a medicament for use in the elevation of PDH activity in warm-blooded animals such as humans.

According to another preferred aspect of the present invention there is provided the use of Example 1 and a pharmaceutically acceptable in vivo cleavable ester of said compound, and a pharmaceutically acceptable salt of said compound or said ester, in the manufacture of a medicament for use in the elevation of PDH activity in warm-blooded animals such as humans.

According to a more preferred aspect of the present invention there is provided the use of a compound selected from Examples 7, 8 and 15 and a pharmaceutically acceptable in vivo cleavable ester of said compound, and a pharmaceutically acceptable salt of said compound or said ester, in the manufacture of a medicament for use in the elevation of PDH activity in warm-blooded animals such as humans.

Compounds of the invention include:
(S)-2-hydroxy-2-methyl-N-(2-nitro-4-phenylsulphonylphenyl)-3,3,3-trifluoropropanamide,
(S)-N-(2-chloro-4-phenylsulphonylphenyl)-2-hydroxy-2-methyl-3,3,3-trifluoropropanamide,
N-(4-cyano-2-methylphenyl)-2-hydroxy-2-methyl-3,3,3-trifluoropropanamide, N-(4-cyano-2-trifluoromethylphenyl)-2-hydroxy-2-methyl-3,3,3-trifluoropropanamide, and Examples 3, 4, 9, 16–26, 34, 35, 40–44 and 48–52 and a pharmaceutically acceptable in vivo cleavable ester of said compound; and a pharmaceutically acceptable salt of said compound or said ester.

Preferred compounds are:

N-(4-cyano-2-methylphenyl)-2-hydroxy-2-methyl-3,3,3-trifluoropropanamide,

N-(4-cyano-2-trifluoromethylphenyl)-2-hydroxy-2-methyl-3,3,3-trifluoropropanamide, and Examples 3, 4, 26 and 49–52 and a pharmaceutically acceptable in vivo cleavable ester of said compound; and a pharmaceutically acceptable salt of said compound or said ester.

More preferred compounds are Examples 22, 24 and 55 and a pharmaceutically acceptable in vivo cleavable ester of said compound; and a pharmaceutically acceptable salt of said compound or said ester.

Particularly preferred compounds are Examples 34 and 35 and a pharmaceutically acceptable in vivo cleavable ester of said compound; and a pharmaceutically acceptable salt of said compound or said ester.

More particularly preferred compounds are Examples 9, 16, 17, 19–21, 23, 40–44 and 48 and a pharmaceutically acceptable in vivo cleavable ester of said compound; and a pharmaceutically acceptable salt of said compound or said ester.

Another more particularly preferred compound of the invention is Example 18 and a pharmaceutically acceptable in vivo cleavable ester of said compound; and a pharmaceutically acceptable salt of said compound or said ester.

Another more particularly preferred compound of the invention is Example 16 and a pharmaceutically acceptable in vivo cleavable ester of said compound; and a pharmaceutically acceptable salt of said compound or said ester.

In another aspect of the invention preferred compounds of the invention include any one of Examples 3–6, 9, and 16–61 and pharmaceutically acceptable in vivo cleavable ester of said compounds and a pharmaceutically acceptable salt of said compounds or said esters.

In a further aspect of the invention preferred compounds of formula (I) or (Ie) include Examples 28, 47 and 55–61 and a pharmaceutically acceptable in vivo cleavable ester of said compound; and a pharmaceutically acceptable salt of said compound or said ester.

Preferred aspects of the invention are those which relate to the compound or a pharmaceutically acceptable salt thereof.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–6 carbon atoms, preferably 1–4 carbon atoms.

In this specification the term "alkoxy" means an alkyl group as defined hereinbefore linked to an oxygen atom.

In this specification the term "aryl" includes $C_{6-10}$ aromatic groups which may, if desired, carry one or more substituents selected from halogeno, alkyl, alkoxy, cyano, nitro or trifluoromethyl (wherein alkyl and alkoxy are as hereinbefore defined). The term "aryloxy" means an aryl group as defined hereinbefore linked to an oxygen atom.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which elevates PDH activity and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated by those skilled in the art that certain compounds of formula (I) contain an asymmetrically substituted carbon and/or sulphur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the elevation of PDH activity, it being well known in the art how to prepare optically-active forms (for example, by resolution of the racemic form by recrystallization techniques, by synthesis from optically-active starting materials, by chiral synthesis, by enzymatic resolution, (for example WO 9738124), by biotransformation, or by chromatographic separation using a chiral stationary phase) and how to determine efficacy for the elevation of PDH activity by the standard tests described hereinafter.

It is also to be understood that certain compounds of the formula (I) and salts thereof can exist in solvated as well as unsolvated forms such as, for example, hydrated forms. It is to be understood that the invention encompasses all such solvated forms which elevate PDH activity.

A compound of the formula (I), or salt thereof, and other compounds of the invention (as hereinafter defined) may be prepared by any process known to be applicable to the preparation of chemically-related compounds. Such processes include, for example, those illustrated in European Patent Applications, Publication Nos. 0524781, 0617010, 0625516, and in GB 2278054, WO 9323358 and WO 9738124.

Such processes, are provided as a further feature of the invention and are as described hereinafter, wherein, unless specified otherwise, Ar, Y, ring C, A—B, $R^1$, $R^2$, $R^3$ and n are as defined hereinbefore. Necessary starting materials may be obtained by standard procedures of organic chemistry. The preparation of such starting materials is illustrated within the accompanying non-limiting Examples. Alternatively necessary starting materials are obtainable by analogous procedures to those illustrated which are within the ordinary skill of an organic chemist.

Thus the following processes constitute further features of the present invention. Compounds of the formula (I) and salts thereof may be prepared:

(a) by deprotecting a protected compound having formula (II):

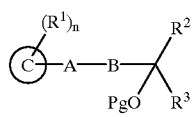
(II)

wherein "Pg" is a suitable alcohol protecting group such as for example a benzyl, acetate or silyl protecting group; examples of suitable reagents for deprotecting a compound of formula (II) when Pg is benzyl are (1) hydrogen in the presence of palladium-on-carbon catalyst, i.e. hydrogenolysis, or (2) hydrogen bromide or iodide; when Pg is acetate diluted inorganic base, for example aqueous lithium-, sodium- or potassium-hydroxide; and when Pg is a silyl protecting group are (1) tetrabutylammonium fluoride, or (2) aqueous hydrofluoric acid. The reaction can be conducted in a suitable solvent such as ethanol, methanol, acetonitrile, or dimethyl sulfoxide (DMSO) and may conveniently be performed at a temperature in the range of −40 to 100° C.;

(b) when Y is carbonyl: by oxidizing a corresponding alcohol of formula (III):

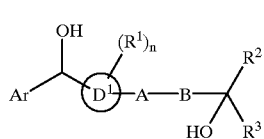
(III)

wherein ring $D^1$ has any of the values defined hereinbefore for ring C but in which the place of one of the possible substituents on ring C is taken by ArCH(OH). Oxidizing agents such as pyridinium dichromate and solvents such as methanol and dichloromethane, respectively, may be employed;

(c) by deprotecting a corresponding compound of formula (I) wherein in place of Y is a ketal protected carbonyl, for example by deprotecting a compound of formula (IV):

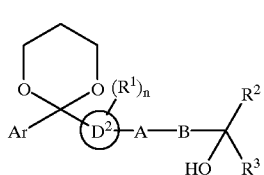
(IV)

wherein ring $D^2$ has any of the values defined hereinbefore for ring C but in which the place of one of the possible substituents on ring C is taken by Ar(—C—O—(CH$_2$)$_3$—O—)—. A saturated aqueous acid such as oxalic or a mineral acid such as hydrochloric acid or sulphuric acid may conveniently be employed. The reaction may conveniently be performed at a temperature in the range of 0 to 100° C. in a solvent such as a lower alcohol (e.g., methanol or ethanol), or mixtures of solvent pairs such as water/dichloromethane, water/tetrahydrofuran, and water/acetone;

(d) by treating a compound of formula (V):

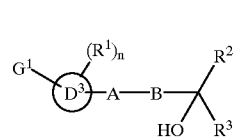
(V)

wherein ring $D^3$ has any of the values defined hereinbefore for ring C but in which the place of one of the possible substituents on ring C is taken by $G^1$ and $G^1$ is defined as a leaving group such as for example bromo, iodo or triflate, with a tin compound having the formula $(R^6)_{p1}Sn(Ar)_{p2}$ (wherein $R^6$ is (1–4C)alkyl such as methyl or butyl and p1+p2=4) and carbon monoxide to effect carbonylative coupling, in the presence of a suitable catalyst such as bis(triphenylphosphine)palladium dichloride. The reaction may conveniently be performed at a temperature in the range of 0 to 100° C. and in a solvent such as tetrahydrofuran, 1,3-dimethyl-3,4,5,6-tetrahydro-2(1H)-pyrimidinone, or DMSO;

(e) by treating a compound of formula (V) wherein $G^1$ is a leaving group such as for example bromo, iodo or triflate, with an aluminium compound having the formula $(R^6)_{p3}Al(Ar)_{p4}$ (wherein $R^6$ is (1–4C)alkyl such as methyl or butyl and p3+p4=3) and carbon monoxide to effect carbonylative coupling, in the presence of a suitable catalyst such as bis(triphenylphosphine)palladium dichloride. The reaction may conveniently be performed at a temperature in the range of 0 to 100° C. and in a solvent such as diethyl ether, benzene, toluene, or tetrahydrofuran;

(f) when Y is sulfonyl: by treating a compound of formula (V), wherein $G^1$ is a leaving group such as for example bromo or iodo, especially iodo, with a compound of formula ArSO$_2^-$Na$^+$ in the presence of a Cu(I) catalyst such as cuprous iodide. The reaction may conveniently be performed at a temperature in the range of 30 to 200° C. and in a solvent such as N,N-dimethylformamide, 1,3-dimethyl-3,4,5,6-tetra-hydro-2(1H)-pyrimidinone, DMSO, or ethylene glycol;

(g) when Y is sulfinyl or sulfonyl and A—B is any of the values defined above, except SCH$_2$ or NHCH$_2$: by oxidizing a compound of formula (V) wherein $G^1$ is ArS. Suitable oxidizing agents include potassium permanganate, OXONE (trade mark of E. I. du Pont de Nemours & Co.,Inc), sodium periodate, tert-butyl hydroperoxide (as solution in toluene), 3-chloroperoxybenzoic acid and hydrogen peroxide. The reaction may be conducted in a suitable solvent such as diethyl ether, dichloromethane, methanol, ethanol, water, acetic acid, or mixtures of two or more of the aforementioned. The reaction may conveniently be performed at a temperature in the range of −40 to 70° C.;

(h) when A—B is NHCO: by coupling a compound of formula (VI):

(VI)

wherein J is $NH_2$ with an acid of formula (VII):

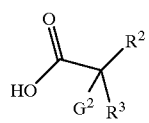

(VII)

wherein $G^2$ is a hydroxy group. The reaction can be conducted in a suitable solvent and in the presence of a suitable coupling reagent. Suitable coupling reagents, for use in situ and generally known in the art as standard peptide coupling reagents, can be employed, for example thionyl chloride, oxalyl chloride, carbonyldiimidazole and dicyclohexyl-carbodiimide, optionally in the presence of a catalyst such as 4-dimethylaminopyridine or 4-pyrrolidinopyridine. A suitable base for this process is for example triethylamine, pyridine, or 2,6-di-alkyl-pyridines such as for example 2,6-lutidine or 2,6-di-tert-butylpyridine. Suitable solvents include dimethylacetamide, dichloromethane, benzene, tetrahydrofuran, and dimethylformamide. The coupling reaction may conveniently be performed at a temperature in the range of −40 to 40° C. The reaction may also be effected using an acid of formula (VII) wherein $G^2$ is protected hydroxy to give a compound of the formula (II) followed by deprotection, (which may be effected by a process as described in (a) above), to give a compound of formula (I);

(i) by coupling a compound of formula (VI) wherein J is $NH_2$ with an activated acid derivative of an acid of formula (VII), wherein $G^2$ is a hydroxy group, such as for example stable acid chlorides, acid anhydrides, or phenylesters in the presence of a base such as for example triethylamine, pyridine, or 2,6-di-alkyl-pyridines such as for example 2,6-lutidine or 2,6-di-tert-butylpyridine. Suitable solvents include dimethylacetamide, dichloromethane, benzene, tetrahydrofuran, and dimethylformamide. The coupling reaction may conveniently be performed at a temperature in the range of −40 to 40° C. The reaction may also be effected using an activated acid derivative of formula (VII) wherein $G^2$ is protected hydroxy to give a compound of the formula (II) followed by deprotection, (which may be effected by a process as described in (a) above), to give a compound of formula (I);

(j) by reacting an amide of formula (VIII):

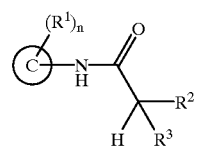

(VIII)

with a base sufficiently basic (e.g., a lithium dialkylamide such as lithium diisopropyl amide) to yield an amide dianion, followed by treatment of the dianion with oxygen in the presence of a reducing agent (e.g., such as triphenylphosphine). The sequence of reactions may conveniently be performed at a temperature in the range of −100 to −20° C., preferably at a temperature in the range of −20 to 50° C., in a suitable solvent such as tetrahydrofuran or diethyl ether;

(k) by reacting a corresponding compound of formula (IX):

(IX)

wherein Hal indicates a halogen substituent (e.g., the corresponding chloride), with a corresponding alkali metal amide dianion having formula (X);

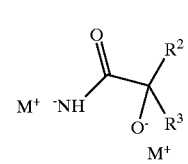

(X)

wherein M is an alkali metal such as sodium or lithium. The reaction may conveniently be performed at a temperature in the range of −40 to 100° C. and in a suitable solvent such as dimethylformamide, DMSO, or tetrahydrofuran;

(l) when Y is sulfonyl and $R^2=R^3$: by reacting a corresponding compound of formula (XI):

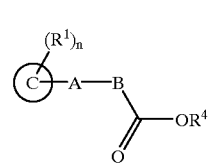

(XI)

wherein $OR^4$ is an alcohol residue such as for example methoxy or ethoxy, with a Grignard compound of formula $R^2MgBr$ or $R^2MgCl$. The reaction may conveniently be performed at a temperature in the range of −100 to 20° C., preferably at a temperature in the range of −20 to 20° C., in a suitable solvent such as tetrahydrofuran or diethyl ether;

(m) when Y is sulfonyl: by treating a corresponding compound of formula (XII):

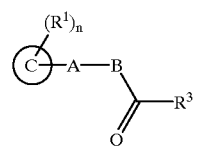

(XII)

with a compound of formula $R^2M$ wherein M is an alkali metal (such as lithium) or a Grignard compound of formula $R^2MgBr$ or $R^2MgCl$. The reaction may conveniently be performed at a temperature in the range of −100 to 0° C. and in a solvent such as tetrahydrofuran, diethyl ether, or 1,2-dimethoxyethane;

(n) when A—B is ethynylene: by coupling a corresponding compound of formula (XIII):

(XIII)

wherein L is a leaving group such as bromo, iodo or triflate, with a corresponding acetylene of formula (XIV):

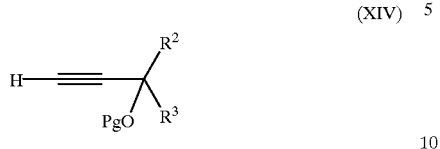

(XIV)

in the presence of a catalyst such as a combination of cuprous iodide and bis(triphenyl-phosphine)palladium dichloride or palladium(II) acetate to give a compound of formula (II). The reaction can be conducted in an inert solvent such as tetrahydrofuran, benzene, or toluene, or in a basic solvent such as diethylamine (DEA) or triethylamine (TEA), and at a temperature in the range of –20 to 110° C. The compound of formula (II) so formed can be deprotected as described in (a) hereinbefore;

(o) by reacting a corresponding alkyne of formula (XV):

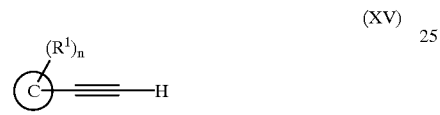

(XV)

with a base such as lithium diisopropylamide (LDA), n-butyllithium or tert-butyllithium, followed by treatment with a ketone of formula $R^3$—CO—$R^2$. The reaction may conveniently be performed at a temperature in the range of –100 to 40° C. preferably at a temperature in the range of –70 to –40° C. and in a solvent such as tetrahydrofuran, diethyl ether, or 1,2-dimethoxyethane;

(p) when A—B is trans-vinylene: by reducing a corresponding acetylene of formula (XVI):

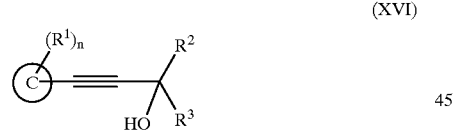

(XVI)

with a suitable reducing agent, for example lithium aluminum hydride. The reaction can be conducted in a suitable solvent such as tetrahydrofuran or diethyl ether, and at a temperature in the range of 0 to 50° C.;

(q) by dehydration of a diol of formula (XVII):

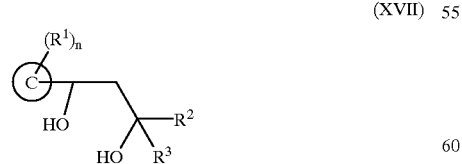

(XVII)

in the presence of an acid catalyst (for example p-toluenesulfonic acid), neat or with a solvent such as toluene or dichloromethane, and at a temperature in the range of 0 to 200° C. preferably a temperature in the range of 20 to 100° C.;

(r) by base catalysed opening of an epoxide of formula (XVIII):

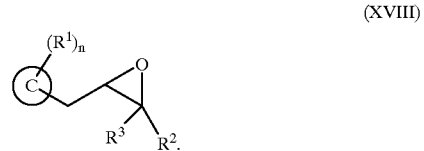

(XVIII)

The opening may be carried out in a suitable organic solvent such as for example, ethers, alcohols, or toluene, of which ethers and toluene are preferred, especially ethers such as tetrahydrofuran. Suitable bases include for example potassium tert-butoxide or sodium hydride. A basic aqueous solution may conveniently be employed. A preferred base is aqueous sodium hydroxide. The opening may be carried out at a temperature in the range of –50° C. to 100° C., preferably at a temperature in the range of 0 to 50° C., such as for example room temperature;

(s) when A—B is NHCH$_2$: by reducing a corresponding compound of formula (I) in which A—B is NHCO, with a suitable reducing agent such as lithium aluminum hydride or borane. The reaction can conveniently be carried out at a temperature in the range of 0° C. to reflux, in solvents such as for example diethyl ether, tetrahydrofuran, or 1,2-dimethoxyethane;

(t) when A—B is OCH$_2$, SCH$_2$ or NHCH$_2$: by reacting an ethylene oxide of formula (XIX):

(XIX)

with a corresponding compound of formula (VI) (wherein J is, correspondingly, oxygen, sulphur or NH), in the presence of a base such as for example sodium hydride. The reaction can be conducted at reflux in a solvent such as dichloromethane;

(u) by heating a corresponding compound of formula (XX):

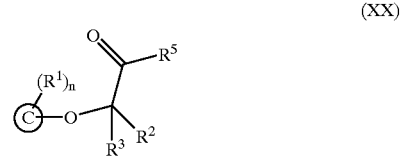

(XX)

wherein $R^5$ is correspondingly, OH, NH$_2$ or SH in the presence of a base such as for example an alkali metal hydride at a temperature in the range of 20° C. to about reflux, in a solvent such as N,N-dimethylformamide;

(v) when Y is sulfonyl, A—B is trans-vinylene or ethynylene, and $R^2$=$R^3$: for a compound of formula (I) which bears a hydroxy substituent on an aryl or heteroaryl group, by cleaving the alkyl ether or acyloxy ester of a corresponding compound of formula (I) which bears a lower alkoxy or lower acyloxy substituent on an aryl or heteroaryl group. Convenient methods include, for example, the cleavage of a methoxy group using boron tribromide and the cleavage of a tert-butoxy group using trifluoroacetic acid;

(w) a compound of formula (I), wherein ring C is substituted by $ArSO_2$, A—B is NHCO and $R^1$ is ortho-nitro may be made from a compound of formula (XXI):

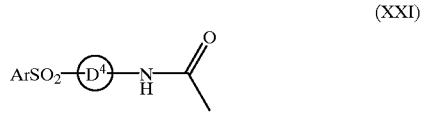

(XXI)

wherein ring $D^4$ has any of the values defined hereinbefore for ring C but in which the place of one of the possible substituents on ring C is taken by $ArSO_2$, (1) on treatment with nitric acid, thereafter (2) treating the nitrated compound under mild alkaline conditions (i.e., employing a base such as lithium hydroxide) to aid the cleavage of the acetate group to yield the desired amine, which can be converted to a compound of formula (II), wherein A—B is NHCO in a manner analogous to that described in procedure (h) or (i) hereinbefore for making an amide, that is, by coupling the amine formed with a corresponding acid or activated acid derivative of formula (VII). The resulting compound of formula (II) may then be deprotected by a process as described in (a) hereinbefore to give a compound of formula (I); and (x) a compound of formula (I), wherein ring C is substituted by ArC=O and A—B is NHCO, may be made by (1) acylation of a compound of formula (VI) wherein J is $NH_2$. Acylating reagents such as benzoic acids, or derivatives thereof, may be employed in the presence of the appropriate activating reagent such as for example polyphosphoric acid. The reaction may conveniently be performed at a temperature in the range of 0 to 200° C. employing a solvent such as N,N-dimethylformamide, 1,3-dimethyl-3,4,5,6-tetra-hydro-2(1H)-pyrimidinone, DMSO, or ethylene glycol if required, followed by (2) the formation of an amide as described in (i) or (j) hereinbefore (Staskum, B., J. Org. Chem. (1964), 29, 2856–2860; Ohnmacht C., J. Med. Chem. (1996), 39, 4592–4601). The compound of formula (II) so formed may then be deprotected for example as described in (a) hereinbefore.

If not commercially available, the necessary starting materials for the procedures such as those described above may be made by procedures which are selected from standard organic chemical techniques, techniques which are analogous to the synthesis of known, structurally similar compounds, or techniques which are analogous to the above described procedure or the procedures described in the examples. In the discussion which follows, "Ar" refers to an unsubstituted or substituted phenyl group or heteroaryl group as previously defined.

In general, a compound of formula (II), wherein AB is $OCH_2$, $SCH_2$ or $NHCH_2$ may be made by treating a corresponding compound of formula (VI) (wherein J is, correspondingly, oxygen, sulphur, or NH) with a corresponding compound of formula (XXII):

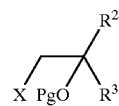

(XXII)

wherein Pg is a protective group such as silyl and X is a suitable leaving group such as for example mesylate or triflate, in the presence of a base such as an alkali metal hydride (e.g., sodium hydride), in a solvent such as tetrahydrofuran, N,N-dimethylformamide, DMSO, or 1,3-dimethyl-3,4,5,6-tetrahydro-2(1H)-pyrimidinone, and at a temperature of about 20° C. to about reflux.

Compounds of formulae (II), (III), (VIII) and (X), wherein A—B is NHCO, may be made in a manner analogous to that described in (h) or (i) above for making an amide of formula (II); that is, by coupling a corresponding amine with a corresponding acid. Thus, to make a protected amide of formula (II), a corresponding amine of formula (VI) may be coupled with an acid of formula (VII) wherein the group corresponding to $G^2$ is O. The protected acid may be made by a conventional procedure, for example by (1) esterifying an acid of formula (VII) wherein $G^2$ is hydroxy by means of a conventional esterification procedure such as reaction with a lower alcohol (e.g., methanol) in the presence of an acid catalyst (for example sulfuric acid) if carboxylate protection is required; (2) reaction of the ester thus formed with an agent which provides the protecting group Pg, such as benzyl chloride (to provide a benzyl protecting group) or any of the conventional silylating agents known and used for such purpose (such as 2-trimethylsilylethoxymethyl chloride, SEM, in the presence of a suitable base such as sodium hydroxide or triethylamine optionally in the presence of a catalyst such as 4-dimethylaminopyridine (DMAP)); and (3) cleavage of the ester group under mild alkaline conditions (i.e., employing a base such as potassium carbonate) to yield the desired protected acid.

If the resolved acid is required it may be prepared by any of the known methods for preparation of optically-active forms (for example, by recrystallization of the chiral salt, by enzymatic resolution, (for example WO 9738124), by biotransformation, or by chromatographic separation using a chiral stationary phase). For example if an (R)-(+) resolved acid is required it may be prepared by the method of Scheme 2 in World Patent Application Publication No. WO 9738124 for preparation of the (S)-(–) acid, ie. using the classical resolution method described in European Patent Application Publication No. EP 0524781, also for preparation of the (S)-(–) acid, except that (1S,2R)-norephedrine may be used in place of(S)-(–)-1-phenylethylamine.

A compound of formula (II) wherein A—B is $OCH_2$, $SCH_2$ or $NHCH_2$ may be made by protecting a corresponding alcohol made in essentially any earlier stage of synthesis, for example an alcohol of formula (V) or (VI). The alcohol may be treated with a compound which reacts to form a trialkylsilyl (e.g. trimethylsilyl) group, such as trimethylsilyl chloride or trimethylsilyl triflate, in the presence of a base such as sodium hydride, diisopropylethylamine or triethylamine. A preferred base is diisopropylethylamine. Alternatively, if an ester protecting group is desired the alcohol may be reacted with an acid chloride of formula $R^7COCl$ or an acid anhydride of formula $(R^7CO)_2O$ wherein $R^7$ is a lower alkyl or aryl group. the reaction may be conducted in a solvent such as dichloromethane, in the presence of a base such as TEA and DMAP, and at a temperature of –40 to about 25° C.

A compound of formula (IV), wherein A—B is ethynylene, may be made by reacting a corresponding compound of formula (XXIII):

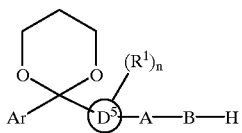

(XXIII)

wherein ring $D^5$ has any of the values defined hereinbefore for ring C but in which the place of one of the possible substituents on ring C is taken by Ar(—C—O—$(CH_2)_3$—O—)— with a base such as an alkyllithium (for example, butyllithium) followed by addition of a ketone having the formula $R^2$—CO—$R^3$. The reaction may be conducted at a temperature of from about −100 to about 40° C. and in a solvent such as tetrahydrofuran, dimethyl ether, or 1,2-dimethoxyethane.

A compound of formula (IV), wherein A—B is trans-vinylene, may be made by reducing a corresponding compound of formula (I), wherein A—B is ethynylene, with a suitable reducing agent such as lithium aluminium hydride or sodium bis(2-methoxyethoxy)aluminium, in a solvent such as tetrahydrofuran and at room temperature.

A compound of formula (II), wherein A—B is trans-vinylene, may be made by reacting a corresponding compound of formula (XXIV):

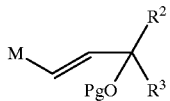

(XXIV)

wherein Pg is a protecting group such as for example benzyl or silyl and M is a metal such as trialkyltin (for example tributyl or trimethyl tin) or bisalkyloxyborane (for example catecholborane), with a compound of formula (IX), wherein Hal may be for example iodide or bromide, in the presence of a catalyst such as bis(triphenylphosphine)palladium dichloride or tetrakistriphenylphosphinepalladium. The reaction may conveniently be conducted in a suitable inert solvent such as a tetrahydrofuran or dimethylformamide at a temperature of from 0–150° C.

A compound of formula (XXIV) may be made by reacting a corresponding alcohol of formula (XXV):

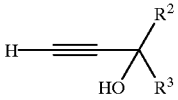

(XXV)

with (1) an agent which provides the protecting group Pg, such as benzyl bromide (to provide a benzyl protecting group) or any of the conventional silylating agents known and used for such purpose (such as for example tert-butyl dimethylsilylchloride or triflate, in the presence of a suitable base such as 1,8-diazabicyclo[5.4.0]undec-7-ene (DBU) or triethylamine optionally in the presence of a catalyst such as DMAP); (2) reaction of the protected propargylic alcohol thus formed with an agent such as catecholborane, to form the vinylborane, or trialkyltin hydride in the presence of a catalytic amount of a radical chain initiator such as for example azo-bis-isobutyronitrile (AIBN), or a strong base such as alkyllithium and copper cyanide, or a transition metal catalyst such as for example tetrakistriphenylphosphinepalladium. The reaction may conveniently be conducted in a suitable inert solvent such as a tetrahydrofuran, toluene or xylene at a temperature of from 0–150° C.

A compound of formula (XXIII) may be made by treating the corresponding ketone with 1,3-propanediol in the presence of an acid catalyst such as p-toluenesulfonic acid (TsOH) and in a refluxing solvent such as toluene.

A compound of formula (XV) may be made by (1) treating a corresponding compound of formula (XIII) wherein L is bromo with a protected acetylene such as trimethylsilylacetylene in the presence of a catalyst such as a combination of cuprous iodide and bis(triphenylphosphine)palladium dichloride in a solvent such as diethylamine, thereby making a corresponding compound of formula (XXVI):

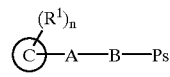

(XXVI)

wherein A—B is ethynylene and Ps is a silyl protecting group, followed by (2) removal of the silyl protecting group with a base such as an alkali metal (e.g. sodium hydroxide) in a solvent such as methanol.

A compound of formula (V) wherein $G^1$ is halo, may be made by (1) treating a corresponding compound of formula (V), wherein $G^1$ is nitro, with a reducing agent such as tin(II)chloride, in the presence of an aqueous acid such as acetic acid to obtain the corresponding amine, followed by (2) treating the amine with a combination of nitric acid and sulfuric acid to effect diazotization, and thereafter (3) treating the diazotized compound with a corresponding copper (I)halide such as for example cuprous bromide.

A compound of formula (V), wherein $G^1$ is SH and A—B is NHCO can be made by (1) coupling of a compound of formula (V) wherein $G^1$ is a leaving group such as halo or triflate with triisopropylsilanethiolate under palladium catalysis as described by Arnould et. al. in Tet. Let. (1996), 37 (26), p. 4523, followed by deprotection with tetrabutylammonium fluoride in a solvent such as tetrahydrofuran at a temperature of −78 to about 25° C.; or (2) by Pummerer rearrangement as described in Tet. Let. (1984), 25 (17), p. 1753 of a compound of formula (V) wherein $G^1$ is $CH_3SO$— and A—B is NHCO, which can be made from a compound of formula (V) wherein $G^1$ is a leaving group such as halo of triflate and A—B is NHCO, using a palladium catalysed coupling with methanethiol as described for example in Zheng et. al. in J. Org. Chem. (1998), 63, p. 9606 followed by an oxidation of the resulting sulphide to the corresponding sulphoxide using for example tert.-butyl hydroperoxide as oxidant; or (3) reduction of a compound of formula (V), wherein $G^1$ is $SO_2Cl$ and A—B is NHCO, by reducing the sulphonyl chloride using a small excess of for example triphenylphosphine in a solvent such as for example dichloromethane in the presence of a catalyst such as for example dimethylforamide, followed by an acidic workup.

A compound of formula (V), wherein $G^1$ is $SO_2Cl$ and A—B is NHCO can be made by treatment with chlorosulphonic acid of a compound of formula (V), wherein $G^1$ is H and A—B is NHCO, under standard conditions.

A compound of formula (XII), wherein A—B is ethynylene, may be made by treating a corresponding compound of formula (XXVI) wherein Ps is trimethylsilyl, with a fluoride base (for example, tetrabutylammonium fluoride (TBAF)) and an acid chloride of formula R³—CO—Cl, thereby making the desired compound.

A compound of formula (XIII), wherein L is halo, may be made by treating a corresponding compound of formula (XIII), wherein L is nitro, with (1) iron dust and concentrated hydrochloric acid in 95% ethanol to reduce the nitro group and thereby form the corresponding amine; (2) the amine may then be treated for example with a nitrite (such as tert-butyl nitrite or sodium nitrite in the presence of a mineral acid) to form the corresponding diazonium salt which may in turn be treated with a copper(I) salt (such as copper(I)bromide or copper(I)chloride). The diazotization and displacement reactions may be conducted, in a solvent such as acetonitrile and at a temperature of from 0 to 25° C.

A compound of formula (XIV) may be made by reacting a corresponding ketone having the formula R²—CO—R³ with an alkali metal acetylide (for example lithium acetylide) or alkaline earth metal acetylide (for example magnesium acetylide). The reaction may be conducted in a solvent such as tetrahydrofuran, diethyl ether, or 1,2-dimethoxyethane and at a temperature of about −100 to about 25° C.

A compound of formula (XV) may be made by reacting a corresponding compound of formula (XIII), wherein L is halo, with trimethylsilylacetylene in the presence of a catalyst such as a combination of bis(triphenylphosphine) palladium dichloride and copper(I)iodide in diethylamine or triethylamine, followed by treatment with a base (for example, an alkali metal hydroxide such as sodium or lithium hydroxide) in a lower alcohol as solvent to effect removal of the trimethylsilyl group.

A compound of formula (XIX) may be made by treating a corresponding ketone having the formula R²—CO—R³ with the ylide derived from the reaction of a trimethylsulfonium salt (such as trimethylsulfonium iodide) with a base (such as an alkali metal hydroxide). The reaction may be conducted in a one-pot process employing a solvent such as dichloromethane.

A compound of formula (VI), wherein J is oxy, may be made by diazotizing a corresponding amine of formula (XIII), wherein L is amino, as previously discussed, and heating in dilute sulfuric acid to form the corresponding phenol. The corresponding thiophenol may be formed by reacting an excess of methanethiol in the presence of sodium hydride with a corresponding compound of formula (XIII) wherein L is a leaving group such as for example chloro.

A compound of formula (XX) wherein R⁵ is hydroxy, thiohydroxy or amino may be made by treating a corresponding compound of formula (XIII) wherein L is a halo group with a corresponding compound of formula (XXII), wherein X is hydroxy, thiohydroxy, or amino, and Pg is hydrogen. The reaction may conveniently be carried out in the presence of a catalyst such as copper bronze and a base such as an alkali metal hydride. The reaction may be conducted at reflux in a solvent such as tetrahydrofuran.

A compound of formula (XXII), wherein X is for example triflate, may be made by (1) esterifying an acid of formula (VII) wherein G² is hydroxy; (2) protecting the alcohol G², by treating with for example trimethylsilyl chloride in a solvent such as dichloromethane and at a temperature of from about −78 to about 25 °C.; (3) treating the protected compound thus obtained with a suitable reducing agent such as lithium aluminum hydride in a solvent such as diethyl ether or tetrahydrofuran and at a temperature of about 0 to about 25° C., thereby reducing the carbonyl group to methylene, followed by (4) treating the reduced product with trifluoromethylsulfonic anhydride in the presence of a base such as triethylamine, in a solvent such as dichloromethane, and at a temperature in the range of about −78 °C. to about 25° C.

An epoxide of formula (XVIII) may be prepared from a diol of formula (XVII) using a suitable dehydrating agent, for example bis[α,α-bis(trifluoromethyl) benzenemethanolato]diphenylsulphur. A diol of formula (XVII) may be prepared from a corresponding compound of formula (I), wherein A—B is CH₂CO, by reduction. The reduction may be carried out using a suitable reducing agent, for example a hydride, such as sodium borohydride.

A corresponding compound of formula (I), wherein A—B is CH₂CO, may be prepared from a compound of formula (XIII), wherein L is methyl, by deprotonation and treatment with an amide of formula (XXVII):

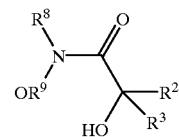

(XXVII)

in which R⁸ and R⁹ are each independently lower alkyl, or in which R⁸ and R⁹ when taken together with the atoms to which they are attached form a 5–7 membered ring. The deprotonation of the toluene may be carried out with a suitable base, for example lithium diisopropyl amide. The reaction may be carried out in a suitable organic solvent, for example, an ether such as tetrahydrofuran. The reaction may be carried out at a suitable temperature, for example a temperature in the range of −78° C. to 100° C.

An amide of formula (XXVII) may be prepared from an acid of formula (VII), wherein G² is hydroxy, or an activated derivative thereof, by reaction with the corresponding amine.

A diol of formula (XVII) may be prepared by (1) treating a ketone of formula (XIII), wherein L is acetyl, with a base such as lithium diisopropylamide, lithium hexamethyldisilazide (LHMDS), or tetramethylpiperadide, in a solvent such as tetrahydrofuran, diethyl ether, or 1,2-dimethoxyethane, followed by addition of a ketone having the formula R²—CO—R³ (aldol addition), and at a temperature of about −100 to about 25° C., followed by (2) reduction of the carbonyl group to alcohol with a reducing agent such as sodium borohydride or lithium aluminum hydride at a temperature of from about 0 to about 25° C.

A corresponding compound of formula (I), wherein ring C is substituted by ArS, A—B is NHCO and R¹ is ortho-halo or ortho-hydroxy, may be made by treatment of a compound of formula (XXVIII):

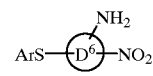

(XXVIII)

wherein ring D⁶ has any of the values defined hereinbefore for ring C but in which the place of one of the possible substituents on ring C is taken by ArS and wherein the amino group is in a position ortho to the nitro group, with (1) a combination of nitric acid and sulphuric acid to effect diazotization, and thereafter (2) treating the diazotized compound with a corresponding copper (I) halide such as for example cuprous bromide or chloride, or heating in dilute sulphuric acid to form the corresponding phenol, followed by (3) reduction of the nitro group with a reducing agent such as tin(II)chloride or iron dust in conjunction with concentrated acid followed by (4) amide formation as described in (h) or (i) hereinbefore. The diazotization and displacement reactions may be conducted in a solvent such as acetonitrile and at a temperature of from 0–25° C.

A compound of formula (XXVIII) may be made for example according to procedures similar to those described in J. Med. Chem., 1975, 18, 1164.

A corresponding compound of formula (I), wherein ring C is substituted by ArS and A—B is NHCO may be made by treatment of a compound of formula (V), wherein $G^1$ is a displaceable group such as halo or triflate, with a thiophenol in the presence of a catalyst such as tetrakis (triphenylphosphine)palladium(0) or cuprous chloride. The reaction may conveniently be conducted in a suitable inert solvent such as a lower alcohol or dimethylformamide and in the presence of a base such as for example sodium methoxide if required.

A corresponding compound of formula (I), wherein ring C is substituted by ArS and A—B is NHCO may be made by treating a compound of formula (V), wherein $G^1$ is SH with an aromatic compound containing a displaceable group such as for example halo or triflate, in the presence of a catalyst such as tetrakis(triphenylphosphine)palladium(0) or cuprous chloride. The reaction may conveniently be conducted in a suitable inert solvent such as a lower alcohol A—E or dimethylformamide and in the presence of a base such as for example sodium methoxide if required at a temperature of 25–180° C.

A corresponding compound of formula (I), wherein ring C is substituted by ArS and A—B is not NHCO may be made by treating a compound of formula (V), wherein $G^1$ is an appropriate leaving group such as for example fluoro, with a compound of formula ArSH in the presence of a suitable base such as for example potassium carbonate. The reaction may conveniently be performed at a temperature in the range of 30 to 200° C. and in a solvent such as N,N-dimethylformamide, 1,3-dimethyl-3,4,5,6-tetra-hydro-2(1H)-pyrimidinone, DMSO, or ethylene glycol.

According to a further feature of the invention, there is provided a process for preparing a compound of formula (Ie) using any one of processes a), f), g), h), i), j), k) or m); and thereafter if necessary:

i) converting a compound of the formula (I) into another compound of the formula (I);

ii) removing any protecting groups; or iii) forming a pharmaceutically acceptable salt or in vivo cleavable ester.

It is noted that many of the starting materials for synthetic methods for intermediates as described above are commercially available and/or widely reported in the scientific literature. If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

In cases where compounds of formula (I) are sufficiently basic or acidic to form stable acid or basic salts, administration of the compound as a salt may be appropriate, and pharmaceutically acceptable salts may be made by conventional methods such as those described following. Examples of suitable pharmaceutically acceptable salts are organic acid addition salts formed with acids which form a physiologically acceptable anion, for example, tosylate, methanesulfonate, acetate, tartrate, citrate, succinate, benzoate, ascorbate, α-ketoglutarate, and α-glycerophosphate. Suitable inorganic salts may also be formed such as sulfate, nitrate, and hydrochloride.

Pharmaceutically acceptable salts may be obtained using standard procedures well known in the art, for example by reacting a sufficiently basic compound of formula (I) (or its ester) with a suitable acid affording a physiologically acceptable anion. It is also possible with most compounds of the invention to make a corresponding alkali metal (e.g., sodium, potassium, or lithium) or alkaline earth metal (e.g., calcium) salt by treating a compound of formula (I) (and in some cases the ester) with one equivalent of an alkali metal or alkaline earth metal hydroxide or alkoxide (e.g. the ethoxide or methoxide in aqueous medium followed by conventional purification techniques.

In vivo cleavable esters of compounds of the invention may be made by coupling with a pharmaceutically acceptable carboxylic acid or an activated derivative thereof. For example, the coupling may be carried out by treating a compound of formula (a) with an appropriate acid chloride (for example, acetyl chloride, propionyl chloride, or benzoyl chloride) or acid anhydride (for example, acetic anhydride, propionic anhydride, or benzoic anhydride) in the presence of a suitable base such as triethylamine. Those skilled in the art will appreciate that other suitable carboxylic acids (including their activated derivatives) for the formation of in vivo cleavable esters are known to the art and these are also intended to be included within the scope of the invention. Catalysts such as 4-dimethylaminopyridine may also be usefully employed.

Many of the intermediates defined herein are novel and these are provided as a further feature of the invention.

The identification of compounds which elevate PDH activity is the subject of the present invention. These properties may be assessed, for example, using one or more of the procedures set out below:

(a) In vitro Elevation of PDH activity

This assay determines the ability of a test compound to elevate PDH activity. cDNA encoding PDH kinase may be obtained by Polymerase Chain Reaction (PCR) and subsequent cloning. This may be expressed in a suitable expression system to obtain polypeptide with PDH kinase activity. For example rat PDHkinaseII (rPDHKII) obtained by expression of recombinant protein in *Escherichia coli* (*E. Coli*), was found to display PDH kinase activity.

In the case of the rPDHKII (Genbank accession number U10357) a 1.3 kb fragment encoding the protein was isolated by PCR from rat liver cDNA and cloned into a vector (for example pQE32—Quiagen Ltd.). The recombinant construct was transformed into *E. coli* (for example M15pRep4—Quiagen Ltd.). Recombinant clones were identified, plasmid DNA was isolated and subjected to DNA sequence analysis. One clone which had the expected nucleic acid sequence was selected for the expression work. Details of the methods for the assembly of recombinant DNA molecules and the expression of recombinant proteins in bacterial systems can be found in standard texts for example Sambrook et al, 1989, Molecular Cloning—A Laboratory Manual, $2^{nd}$ edition, Cold Spring Harbour Laboratory Press. Other known PDH kinases for use in assays, may be cloned and expressed in a similar manner.

For expression of rPDHKII activity, *E. coli* strain M15pRep4 cells were transformed with the pQE32 vector containing rPDHKII cDNA. This vector incorporates a 6-His tag onto the protein at its N-terminus. *E. coli* were grown to an optical density of 0.6 (600 nM) and protein expression was induced by the addition of 10 μM isopropylthio-β-galactosidase. Cells were grown for 18 hours at 18° C. and harvested by centrifugation. The resuspended cell paste was lysed by homogenisation and insoluble material removed by centrifugation at 24000×g for 1 hour. The 6-His tagged protein was removed from the supernatant using a nickel chelating nitrilotriacetic acid resin (Ni-NTA: Quiagen Ltd.) matrix (Quiagen) which was washed with 20 mM tris(hydroxymethyl)aminomethane-hydrogen chloride, 20 mM imidazole, 0.5 M sodium chloride pH 8.0, prior to elution of bound protein using a buffer containing 20 mM tris(hydroxymethyl)aminomethane-hydrogen chloride, 200 mM imidazole, 0.15 M sodium chloride pH 8.0. Eluted fractions containing 6-His protein were pooled and stored in aliquots at −80° C. in 10% glycerol.

Each new batch of stock enzyme was titrated in the assay to determine a concentration giving approximately 90% inhibition of PDH in the conditions of the assay. For a typical batch, stock enzyme was diluted to 7.5 μg/ml.

For assay of the activity of novel compounds, compounds were diluted with 10% dimethylsulphoxide (DMSO) and 10 μl transferred to individual wells of 96-well assay plates. Control wells contained 20 μl 10% DMSO instead of compound. 40 μl Buffer containing 50 mM potassium phosphate buffer pH 7.0, 10 mM ethylene glycol-bis(β-aminoethyl ether)-N,N,N,N-tetracetic acid (EGTA), 1 mM benzamidine, 1 mM phenylmethylsulphonyl fluoride (PMSF), 0.3 mM tosyl-L-lysine chloromethyl ketone (TLCK), 2 mM dithiothreitol (DTT), recombinant rPDHKII and compounds were incubated in the presence of PDH kinase at room temperature for 45 minutes. In order to determine the maximum rate of the PDH reaction a second series of control wells were included containing 10% DMSO instead of compound and omitting rPDHKII. PDH kinase activity was then initiated by the addition of 5 μM ATP, 2 mM magnesium chloride and 0.04 U/ml PDH (porcine heart PDH Sigma P7032) in a total volume of 50 μl and plates incubated at ambient temperature for a further 45 minutes. The residual activity of the PDH was then determined by the addition of substrates (2.5 mM coenzyme A, 2.5 mM thiamine pyrophosphate (cocarboxylase), 2.5 mM sodium pyruvate, 6 mM NAD in a total volume of 80 μl and the plates incubated for 90 minutes at ambient temperature. The production of reduced NAD (NADH) was established by measured optical density at 340 nm using a plate reading spectrophotometer. The $ED_{50}$ for a test compound was determined in the usual way using results from 12 concentrations of the compound.

(b) In vitro Elevation of PDH Activity in Isolated Primary Cells

This assay determines the ability of compounds to stimulate pyruvate oxidation in primary rat hepatocytes.

Hepatocytes were isolated by the two-step collagenase digestion procedure described by Seglen (Methods Cell Biol. (1976) 13, 29–33) and plated out in 6-well culture plates (Falcon Primaria) at 600000 viable cells per well in Dulbecco's Modified Eagles Medium (DMEM, Gibco BRL) containing 10% foetal calf serum (FCS), 10% penicillin/streptomycin (Gibco BRL) and 10% non-essential amino acids (NEAA, Gibco BRL). After 4 hours incubation at 37° C. in 5% $CO_2$, the medium was replaced with Minimum Essential Medium (MEM, Gibco BRL) containing NEAA and penicillin/streptomycin as above in addition to 10 nM dexamethasone and 10 nM insulin.

The following day cells were washed with phosphate buffered saline (PBS) and medium replaced with 1 ml HEPES-buffered Krebs solution (25 mM HEPES, 0.15M sodium chloride, 25 mM sodium hydrogen carbonate, 5 mM potassium chloride, 2 mM calcium chloride, 1 mM magnesium sulphate, 1 mM potassium dihydrogen phosphate) containing the compound to be tested at the required concentration in 0.1% DMSO. Control wells contained 0.1% DMSO only and a maximum response was determined using a 10 μM treatment of a known active compound. After a preincubation period of 40 minutes at 37° C. in 5% $CO_2$, cells were pulsed with sodium pyruvate to a final concentration of 0.5 mM (containing 1-$^{14}$C sodium pyruvate (Amersham product CFA85) 0.18 Ci/mmole) for 12 minutes. The medium was then removed and transferred to a tube which was immediately sealed with a bung containing a suspended centre well. Absorbent within the centre well was saturated with 50% phenylethylamine, and $CO_2$ in the medium released by the addition of 0.2 μl 60% (w/v) perchloric acid (PCA). Released $^{14}CO_2$ trapped in the absorbent was determined by liquid scintillation counting. The $ED_{50}$ for a test compound was determined in the usual way using results from 7 concentrations of the compound.

(c) In vivo Elevation of PDH Activity

The capacity of compounds to increase the activity of PDH in relevant tissues of rats may be measured using the test described hereinafter. Typically an increase in the proportion of PDH in its active, nonphosphorylated form may be detected in muscle, heart, liver and adipose tissue after a single administration of an active compound. This may be expected to lead to a decrease in blood glucose after repeated administration of the compound. For example a single administration of DCA, a compound known to activate PDH by inhibition of PDH kinase (Whitehouse, Cooper and Randle (1974) Biochem. J. 141, 761–774) 150 mg/kg, intraperitoneally, increased the proportion of PDH in its active form (Vary et al. (1988) Circ. Shock 24, 3–18) and after repeated administration resulted in a significant decrease in plasma glucose (Evans and Stacpoole (1982) Biochem. Pharmacol.31, 1295–1300).

Groups of rats (weight range 140–180 g) are treated with a single dose or multiple doses of the compound of interest by oral gavage in an appropriate vehicle. A control group of rats is treated with vehicle only. At a fixed time after the final administration of compound, animals are terminally anaesthetised, tissues are removed and frozen in liquid nitrogen. For determination of PDH activity, muscle samples are disrupted under liquid nitrogen prior to homogenisation by one thirty-second burst in a Polytron homogenizer in 4 volumes of a buffer containing 40 mM potassium phosphate pH 7.0, 5 mM EDTA, 2 mM DTT, 1% Triton X-100, 10 mM sodium pyruvate, 10 μM phenylmethylsulphonyl chloride (PMSF) and 21 μg/ml each of leupeptin, pepstain A and aprotinin. Extracts are centrifuged before assay. A portion of the extract is treated with PDH phosphatase prepared from pig hearts by the method of Siess and Wieland (Eur. J. Biochem (1972) 26, 96): 20 μl extract, 40 μl phosphatase (1:20 dilution), in a final volume of 125 μl containing 25 mM magnesium chloride, 1 mM calcium chloride. The activity of the untreated sample is compared with the activity of the dephosphorylated extract thus prepared. PDH activity is assayed by the method of Stansbie et al., (Biochem. J. (1976) 154, 225). 50 μl Extract is incubated with 0.75 mM NAD, 0.2 mM CoA, 1.5 mM thiamine pyrophosphate (TPP) and 1.5 mM sodium pyruvate in the presence of 20 μg/ml p-(p-amino-phenylazo) benzene sulphonic acid (AABS) and 50 mU/ml arylamine transferase (AAT) in a buffer containing 100 mM tris(hydroxymethyl)aminomethane, 0.5 mM EDTA, 50 mM sodium fluoride, 5 mM 2-mercaptoethanol and 1 mM magnesium chloride pH 7.8. AAT is prepared from pigeon livers by the method of Tabor et al. (J. Biol. Chem. (1953) 204, 127). The rate of acetyl CoA formation is determined by the rate of reduction of AABS which is indicated by a decrease in optical density at 460 nm.

Liver samples are prepared by an essentially similar method, except that sodium pyruvate is excluded from the extraction buffer and added to the phosphatase incubation to a final concentration of 5 mM.

Treatment of an animal with an active compound results in an increase in the activity of PDH complex in tissues. This is indicated by an increase in the amount of active PDH (determined by the activity of untreated extract as a percentage of the total PDH activity in the same extract after treatment with phosphatase).

According to a further aspect of the invention there is provided a pharmaceutical composition which comprises a compound of the formula (I) as defined hereinbefore or a pharmaceutically acceptable in vivo cleavable ester of said compound of formula (I) or a pharmaceutically acceptable salt of said compound or said ester, in association with a pharmaceutically acceptable excipient or carrier.

According to an additional aspect of the invention there is provided a pharmaceutical composition which comprises a compound of the formula (Ie) as defined hereinbefore or a pharmaceutically acceptable in vivo cleavable ester of said compound of formula (Ie) or a pharmaceutically acceptable salt of said compound or said ester, in association with a pharmaceutically acceptable excipient or carrier.

According to an additional further aspect of the invention there is provided a pharmaceutical composition which comprises a compound selected from N-(4-benzoyl-2,6-dimethylphenyl)-2-hydroxy-2-methyl-3,3,3-trifluoropropanamide or 3-hydroxy-3-trifluoromethyl-1-(2-chloro-5-trifluoromethylphenyl)-4,4,4-trifluorobut-1-yne or a pharmaceutically acceptable in vivo cleavable ester of said compound or a pharmaceutically acceptable salt of said compound or said ester, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula (I) or a pharmaceutically acceptable in vivo cleavable ester of said compound of formula (I) or a pharmaceutically acceptable salt of said compound or said ester as defined hereinbefore for use in a method of treatment of the human or animal body by therapy.

We have found that compounds of the present invention elevate PDH activity and are therefore of interest for their blood glucose-lowering effects.

A further feature of the present invention is a compound of formula (I) or a pharmaceutically acceptable in vivo cleavable ester of said compound of formula (I) or a pharmaceutically acceptable salt of said compound or said ester for use as a medicament, conveniently a compound of formula (I) or a pharmaceutically acceptable in vivo cleavable ester of said compound of formula (I);
or a pharmaceutically acceptable salt of said compound or said ester for use as a medicament for producing an elevation of PDH activity in a warm-blooded animal such as a human being.

Thus according to a further aspect of the invention there is provided the use of a compound of the formula (I) or a pharmaceutically acceptable in vivo cleavable ester of said compound of formula (I) or a pharmaceutically acceptable salt of said compound or said ester in the manufacture of a medicament for use in the production of an elevation of PDH activity in a warm-blooded animal such as a human being.

According to a further feature of the invention there is provided a method for producing an elevation of PDH activity in a warm-blooded animal, such as a human: being, in need of such treatment which comprises administering to said animal an effective amount of a compound of formula (a) or a pharmaceutically acceptable in vivo cleavable ester of said compound of formula (I) or a pharmaceutically acceptable salt of said compound or said ester as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The elevation of PDH activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. For example in the treatment of diabetes mellitus chemotherapy may include the following main categories of treatment:

i) insulin;
ii) insulin secretagogue agents designed to stimulate insulin secretion (for example glibenclamide, tolbutamide, other sulphonylureas);
iii) oral hypoglycaemic agents such as metformin, thiazolidinediones;
iv) agents designed to reduce the absorption of glucose from the intestine (for example acarbose);
v) agents designed to treat complications of prolonged hyperglycaemia;
vi) other agents used to treat lactic acidaemia;
vii) inhibitors of fatty acid oxidation;
viii) lipid lowering agents;
ix) agents used to treat coronary heart disease and peripheral vascular disease such as aspirin, pentoxifylline, cilostazol; and/or
x) thiamine.

As stated above the compounds defined in the present invention are of interest for their ability to elevate the activity of PDH. Such compounds of the invention may therefore be useful in a range of disease states including diabetes mellitus, peripheral vascular disease, (including intermittent claudication), cardiac failure and certain cardiac myopathies, myocardial ischaemia, cerebral ischaemia and reperfusion, muscle weakness, hyperlipidaemias, Alzheimers Disease and/or atherosclerosis.

In addition to their use in therapeutic medicine, the compounds of formula (I) and their pharmaceutically acceptable salts are also useful as pharmacological tools in the development and standardisation of in vitro and in vivo test systems for the evaluation of the effects of elevators of PDH activity in laboratory animals such as cats, dogs, rabbits, monkeys, rats and mice, as part of the search for new therapeutic agents.

It is to be understood that where the term "ether" is used anywhere in this specification it refers to diethyl ether.

EXAMPLES

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C. and under an atmosphere of an inert gas such as argon;

(ii) organic solutions were dried over anhydrous magnesium sulphate; evaporation of solvent was carried out using a rotary evaporator under reduced pressure (600–4000 pascals; 4.5–30 mmHg) with a bath temperature of up to 60° C.;

(iii) chromatography means flash chromatography on silica gel; thin layer .) chromatography (TLC) was carried out on silica gel plates; where a silica Mega Bond Elut column is referred to, this means a column containing 10 g or 20 g of silica of 40 micron particle size, the silica being contained in a 60 ml disposable syringe and supported by a porous disc, obtained from Varian, Harbor City, Calif., USA under the name "Mega Bond Elut SI", "Mega Bond Elut" is a trademark;;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra and/or mass spectral data;

(vii) yields are given for illustration only and are not necessarily those which can be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated; coupling constants (J) are given in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported;

(xiii) unless stated otherwise compounds containing an asymmetrically substituted carbon and/or sulphur atom have not been resolved;

(xiv) where a synthesis is described as being analogous to that described in a previous example the amounts to be used are the millimolar equivalents to those used in the previous example;

(xv) where a Chem Elut column is referred to, this means a "Hydromatrix" extraction cartridge for adsorption of aqueous material, i.e. a polypropylene tube containing a special grade of flux-calcined, high purity, inert diatomaceous earth, pre-buffered to pH 4.5 or 9.0, incorporating a phase-separation filtering material, used according to the manufacturers instructions, obtained from Varian, Harbor City, Calif., USA under the name of "Extube, Chem Elut", "Extube" is a trademark;

(xvi) the following abbreviations have been used:

| | |
|---|---|
| DMF | N,N-dimethylformamide; |
| DMSO | dimethylsulphoxide; |
| DMA | N,N-dimethylacetamide; |
| THF | tetrahydrofuran; and |
| EA | elemental analysis. |

Example 1

N-(4-Benzoyl-2-methylphenyl)-2-hydroxy-2-methyl-3,3,3-trifluoropropanamide (Example 1 of EP 0617010)

To a solution of 2-hydroxy-2-methyl-3,3,3-trifluoropropanamide acid (1.11 g) in DMA (15 ml) at −20° C. was added thionyl chloride (0.84 g) and the mixture was allowed to stir at −10 to −15° C. for 1 hour. 4-Amino-3-methylbenzophenone (1.00 g), (J. Chem. Soc., 1952, 2205–2210), was added in one portion and the reaction mixture was stirred at ambient temperature overnight. The mixture was poured into water and the resultant gummy solid was collected by filtration. The solid was dissolved in dichloromethane, dried and evaporated to give a brown oil. Chromatography, with ether/dichloromethane (2/98) as the eluent, gave a white foam which was stirred with hexane for 2 hours. The title compound was collected by filtration as a white solid (1.04 g). M.p. 123–124° C.; MS: 352 (M+H); NMR: 1.61 (s, 3H), 2.28 (s, 3H), 7.54–7.61 (m, 3H) 7.66–7.74 (m, 6H) 9.73 (s, 1H); EA: $C_{18}H_{16}F_3NO_3$ requires: C, 61.54; H, 4.59; N, 3.99%; found: C, 61.53; H, 4.73; N, 4.01%.

Example 2

N-(4-Benzoyl-2-fluorophenyl)-2-hydroxy-2-methyl-3 3 3-trifluoropropanamide (Example 2 of EP 0617010)

To a solution of 2-hydroxy-2-methyl-3,3,3-trifluoropropanamide acid (4.51 g) in DMA (60 ml) at −20° C. was added thionyl chloride (3.39 g) and the mixture was allowed to stir at −10 to −15° C. for 1 hour. 4-Amino-3-fluorobenzophenone (Method 1) (4.00 g) was added in one portion and the reaction mixture was stirred at ambient temperature overnight. The mixture was poured into water and the aqueous solution was decanted. The remaining oily precipitate was dissolved in dichloromethane, dried, and evaporated to yield a tan solid. Recrystallization from dichloromethane and hexanes yielded the title compound as a white solid (5.43 g). M.p. 138–139° C.; MS: 356(M+H); NMR: 1.62 (s, 3H), 7.56–7.64 (m, 4H), 7.70 (d, 1H. J=6.5), 7.75 (d, 2H, J=8.0), 7.82 (s, 1H), 8.01 (t, 1H, J=7.9), 9.39 (s, 1H); EA: $C_{17}H_{13}F_4NO_3$ requires C, 57.47; H, 3.69; N, 3.94%; found: C, 57.51; H, 3.60; N, 3.93%.

Examples 3–6

Following the procedure of Example 2 and using the appropriate starting material the following compound was prepared.

chromatography, with trichloromethane as the eluent, to yield the title compound as a pale yellow solid (0.46 g). M.p. 191–192.5° C.; MS: 419 (M+H); NMR: 1.58 (s, 3H), 7.63–7.76 (m, 3H), 8.02–8.07 (d, 3H), 8.34 (dd, 1H, J=2.2, 8.6), 8.59 (s, 1H), 8.61 (d, 1H, J=2.3); EA: $C_{16}H_{13}F_3N_2O_6S$ requires C, 45.94; H, 3.13; N, 6.70%; Found: C, 45.95; H, 3.19; N, 6.53%.

| EX | COMPOUND | EA | M.p. |
|---|---|---|---|
| 3[1] | N-(2-Chloro-4-nitrophenyl)-2-hydroxy-2-methyl-3,3,3-trifluoropropanamide | $C_{10}H_8ClF_3N_2O_4$ requires C, 38.4; H, 2.5; N, 9.0%; found: C, 38.9; H, 2.9; N, 8.6%. | 124–125° C. |
| 4[2] | 2-Hydroxy-2-methyl-N-(2-methyl-4-nitrophenyl)-3,3,3-trifluoropropanamide | $C_{11}H_{11}F_3N_2O_4$ requires C, 45.2; H, 3.8; N, 9.6%; found: C, 45.0; H, 4.2; N, 9.2% | 123–125° C. |
| 5[3] | N-(4-Cyano-2-methylphenyl)-2-hydroxy-2-methyl-3,3,3-trifluoropropanamide | $C_{12}H_{11}F_3N_2O_2$ requires C, 52.9; H, 4.0; N, 10.3%; found: C, 52.9; H, 4.1; N, 10.4% | 164–165° C. |
| 6[1] | N-(4-Cyano-2-trifluoromethylphenyl)-2-hydroxy-2-methyl-3,3,3-trifluoropropanamide | $C_{12}H_8F_6N_2O_2$ requires C, 44.2; H, 2.45; N, 8.6%; found: C, 43.8; H, 2.4; N, 8.7%. | 121–123° C. |

[1]Purification was by chromatography on Florisil, (Trade Mark of U.S. Silica Co.), eluting with 0–20% ethyl acetate/toluene then recrystallisation from toluene-hexanes
[2]Purification was by recrystallisation from toluene-hexanes
[3]Aniline ref.: J. Med. Chem., 1991, 34, 3295–3301 and the reaction mixture was poured into ice-water and the resultant solid recrystallized from toluene.

Example 7

2-Hydroxy-N-[2-methoxy-4-(pyrid-4-ylsulphonyl) phenyl]-2-methyl-3,3,3-trifluoropropanamide (Example 4 of EP 0617010)

To a stirred, cooled (−20° C.) solution of 2-hydroxy-2-methyl-3,3,3-trifluoropropanoic acid (1.35 g) in DMA (20 ml) was rapidly added thionyl chloride (1.01 g) and the mixture (a precipitate formed after a few minutes) was stirred at −15 to −5° C. for 1 hour. 2-Methoxy-4-(pyrid-4-ylsulphonyl)aniline (Method 2) (1.50 g) was then added in one portion and the mixture allowed to stir at ambient temperature overnight. The solution was poured into ice water (200 ml) and the resulting tan solid was collected and recrystallized from absolute ethanol to yield the title compound as a white solid (1.58 g). M.p. 220–222° C.; MS: 405 (M+H); NMR (250 MHz): 1.53 (s, 3H), 4.02 (s, 3H), 7.62 (d, 1H, J=1.9), 7.68 (dd, 1H, J=1.9, J=8.5), 7.92–7.95 (m, 2H), 8.02 (s, 1H), 8.46 (d, 1H, J=10) 8.80–8.89 (m, 2H), 9.90 (s, 1H); EA: $C_{16}H_{15}F_3N_2O_5S$ requires C, 47.53; H, 3.74; N, 6.93%; found: C, 47.56; H, 3.77; N, 6.76%.

Example 8

2-Hydroxy-2-methyl-N-[2-nitro-4-(phenylsulphonyl) phenyl]-3,3,3-trifluoropropanamide (Example 5 of EP 0617010)

A mixture of 2-hydroxy-2-methyl-3,3,3-trifluoropropanoic acid (1.00 g), 1,1'-carbonyldiimidazole (1.03 g) and dry THF (25 ml) was heated, under nitrogen, at 45° C. in an ultrasound bath for 0.5 hour. 2-Nitro-4-(phenylsulphonyl)aniline (1.75 g), (DE 2215733), was added, the mixture was heated at 45° C. for 18 hours, poured onto water (350 ml) and extracted with ether. The combined extracts were washed (brine), dried and evaporated to give an orange solid (3.01 g) that was purified by

Example 9

Following the procedure of Example 8 and using (R)-(+)-2-hydroxy-2-methyl-3,3,3-trifluoropropanoic acid the following compound was prepared.

| EX | COMPOUND | NMR | MS |
|---|---|---|---|
| 9[1] | (R)-2-Hydroxy-2-methyl-N-[2-nitro-4-(phenylsulphonyl)-phenyl]-3,3,3-trifluoropropanamide | 1.55 (s, 3H), 7.63 (t, 2H), 7.72 (t, 1H), 8.0 (d, 3H), 8.3 (dd, 1H), 8.58 (m, 2H), 11.53 (br s, 1H) | 262 (M-H)⁻ |

[1]The reaction was carried out for 36 hours at 55° C. and the product was purified by chromatography on a silica gel Mega Bond Elut column eluting with 0–40% ethyl acetate/hexane

Example 10

N-(4-Benzoyl-2-chlorophenyl)-2-hydroxy-2-methyl-3,3,3-trifluoropropanamide (Example 7 of EP 0617010)

To a stirred, cooled (−20° C.) solution of 2-hydroxy-2-methyl-3,3,3-trifluoropropanoic acid (0.46 g) in DMA (6 ml) was rapidly added thionyl chloride (0.35 g) and the mixture stirred at −15 to 20° C. for 1 hour. 4-Amino-3-chlorobenzophenone (0.45 g), (J. Org. Chem., 1962, 27, 1605–1608), was then added in one portion and the mixture allowed to stir at ambient temperature overnight. The solution was poured into ice water and filtered through diatomaceous earth. The diatomaceous earth was washed with dichloromethane, the organic solution dried and the solvent removed. Chromatography (eluent dichloromethane, then 5% ethyl acetate in dichloromethane) gave the title compound (0.31 g) as a white solid. M.p. 142–144° C.; EA $C_{17}H_{13}ClF_3NO_3$ requires C, 54.92; H, 3.53; N, 3.77%; Found: C, 54.89; H, 3.63; N, 3.68%.

Example 11

N-(4-Benzoyl-2-bromophenyl)-2-hydroxy-2-methyl-3,3,3-trifluoropropanamide

(Example 9 of EP 0617010)

To a stirred, cooled (−20° C.) solution of 2-hydroxy-2-methyl-3,3,3-trifluoropropanoic acid (0.75 g) in DMA (10 ml) was rapidly added thionyl chloride (0.56 g) and the mixture stirred at −15 to −20° C. for 1 hour. 4-Amino-3-bromobenzophenone (0.75 g), (J. Med. Chem., 1996, 39, 4592–4601), was then added in one portion and the mixture was allowed to stir at ambient temperature overnight. The solution was poured into ice water and the aqueous phase decanted from the resulting oily solid. Chromatography (eluent dichloromethane) gave the title compound (0.43 g) as a white solid. M.p. 138–40° C.; EA: $C_{17}H_{13}BrF_3NO_3$ requires C, 49.06; H, 3.15; N, 3.37%; Found: C, 49.06; H, 3.10; N, 3.35%.

Example 12

N-(4-Benzoyl-2-cyanophenyl)-2-hydroxy-2-methyl-3,3,3-trifluoropropanamide

(Example 10 of EP 0617010)

To a stirred, cooled solution of 2-hydroxy-2-methyl-3,3,3-trifluoropropanoic acid (0.15 g) in dichloromethane (10 ml) was added thionyl chloride (0.12 g) and the mixture was stirred at reflux for 3 hours. The mixture was cooled to ambient temperature, triethylamine (0.11 g) added and the mixture stirred at reflux for 0.5 hour. The mixture was again cooled to ambient temperature, 4-amino-3-cyanobenzophenone (Method 5) (0.19 g) in THF (2.5 ml) was added and the mixture stirred at reflux overnight. The solvent was evaporated and the residue partitioned between ethyl acetate and 3M hydrochloric acid. The organic layer was washed with water, dried and evaporated to yield a pale yellow oil. Chromatography (eluent dichloromethane then 2% ether in dichloromethane) gave the title compound (0.11 g.) as a white solid. M.p. 202–204° C.; EA: $C_{18}H_{13}F_3N_2O_3$ $0.5H_2O$ requires C, 58.22; N, 7.54%; found: C, 58.03; H, 3.57; N, 7.26%.

Example 13

N-(4-Benzoyl-2-methoxyphenyl)-2-hydroxy-2-methyl-3,3,3-trifluoropropanamide

(Example 11 of EP0617010)

To a stirred, cooled (−20° C.) solution of 2-hydroxy-2-methyl-3,3,3-trifluoropropanoic acid (0.52 g) in DMA (5 ml) was rapidly added thionyl chloride (0.39 g) and the mixture stirred at −10 to −20° C. for 1 hour. 4-Amino-3-methoxybenzophenone (0.50 g), (J. Org. Chem., 1962, 27, 1605–1608) was then added in one portion and the mixture allowed to stir at ambient temperature overnight. The solution was poured into water and the aqueous phase decanted from the resulting oily solid. Chromatography (eluent dichloromethane then 2% ether in dichloromethane) gave the title compound (0.37 g) as an off-white solid. M.p. 126–128° C.; EA: $C_{18}H_{16}F_3NO_4$ $0.25H_2O$ requires C, 58.14; H, 4.47; N, 3.77%; Found: C, 58.29; H, 3.78%.

Example 14

N-(4-Benzoyl-2-hydroxyphenyl)-2-hydroxy-2-methyl-3,3,3-trifluoropropanamide

(Example 12 of EP 0617010)

To a stirred, cooled (−20° C.) solution of 2-hydroxy-2-methyl-3,3,3-trifluoropropanoic acid (1.11 g) in DMA (15 ml) was rapidly added thionyl chloride (0.84 g) and the mixture stirred at −10 to −20° C. for 1 hour. 4-Amino-3-hydroxybenzophenone (1.0 g), (Synthesis, 1990, 679–680), was then added in one portion and the mixture allowed to stir at ambient temperature overnight. The solution was poured into ice water and the aqueous phase decanted from the resulting oily precipitate. Chromatography (eluent 2% to 5% methanol gradient in dichloromethane) yielded a white foam which was dissolved in a small amount of dichloromethane and added dropwise to stirred hexane (100 ml) to yield the title compound (0.86 g) as a white solid. M.p. 119–121° C.; EA: $C_{17}H_{14}F_3NO_4$ requires C, 57.79; H, 3.99; N, 3.96%: Found: C, 57.85; H, 4.39; N, 3.72%.

Example 15

2-Hydroxy-N-[2-hydroxy-4-(pyrid-4-ylsulphonyl)phenyl]-2-methyl-3,3,3-trifluoropropanamide

(Example 13 of EP 0617010)

To a stirred suspension of 2-hydroxy-N-[2-methoxy-4-(pyrid-4-ylsulphonyl)phenyl]-2-methyl-3,3,3-trifluoropropanamide (Example 7) (1.30 g) and molecular sieve dried dichloromethane (50 ml) was added boron tribromide (1.6 ml of a 10M solution in dichloromethane), and the mixture (a gummy ball of material and solvent) was stirred at reflux for 2 hours and then stirred overnight at ambient temperature. The reaction mixture was poured into water, made basic with saturated sodium hydrogen carbonate solution and extracted with dichloromethane (2×250 ml; discarded) followed by ethyl acetate (100 ml). The ethyl acetate solution was dried, filtered, evaporated to a brown oil and purified by chromatography twice (eluent ethyl acetate and eluent dichloromethane/ethyl acetate (¼)) to yield the title compound (0.15 g). M.p. 218–220° C.; EA: $C_{15}H_{13}F_3N_2O_5S$ requires C, 46.16; H, 3.36; N, 7.18%: Found: C, 45.87; H, 3.47; N, 6.91%.

Example 16

(R)-N-[2-Fluoro-4-(phenylsulphonyl)phenyl]-2-hydroxy-2-methyl-3,3,3-trifluoropropanamide

Hydrogen peroxide (0.2 ml of a 30 wt. % solution in water) was added to a solution of (R)-N-[2-fluoro-4-(phenylthio)phenyl]-2-hydroxy-2-methyl-3,3,3-trifluoropropanamide (Method 7) (0.212 g) in glacial acetic acid (0.5 ml) and the mixture was stirred and heated at 100° C. for 75 minutes then allowed to cool. Ethyl acetate (20 ml) was added and the solution was washed with water (20 ml), saturated sodium hydrogen carbonate solution (10 ml) and brine and then dried. Volatile material was removed by evaporation and the residue was purified by chromatography on a silica gel Mega Bond Elut column eluting with 20–30% ethyl acetate/hexane to give the title compound (0.155 g) as a solid. M.p. 121–122° C.; NMR: 1.58 (s, 3H), 7.58–7.7 (m, 4H), 7.8 (d, 1H), 7.9–8.05 (m, 4H), 9.8 (brs, 1H); MS: 390 (M−H)⁻; EA: $C_{16}H_{13}F_4NO_4S$ $0.5H_2O$ requires C, 48.0; H, 3.5; N, 3.5%; found: C, 47.8; H, 3.5; N, 3.4%.

Examples 17–33

Following the procedure of Example 16 and using the appropriate starting materials the following compounds were prepared. "Meth" relates to the method used to make the starting materials (see below).

| EX | COMPOUND | NMR | MS | Meth |
|---|---|---|---|---|
| 17 | (R)-N-[2-Chloro-4-(2-methyl-phenylsulphonyl)phenyl]-2-hydroxy-2-methyl-3,3,3-trifluoropropanamide | 1.6 (s, 3H), 2.4 (s, 3H), 7.4 (d, 1H), 7.5 (t, 1H), 7.62 (t, 1H), 7.88 (dd, 1H), 7.98 (d, 1H), 8.1 (d, 1H), 8.3 (d, 1H) | 420 (M − H)$^-$ | 8a |
| 18 | (R)-2-Hydroxy-2-methyl-N-[2-methyl-4-(phenylsulphonyl)phenyl]-3,3,3-trifluoropropanamide | 1.55 (s, 3H), 2.25 (s, 3H), 7.55–7.67 (m, 4H), 7.72 (d, 1H), 7.8 (dd, 1H), 7.85 (brs, 1H), 7.92 (m, 2H), 9.7 (brs, 1H) | 386 (M − H)$^-$ | 8b |
| 19[1] | (R)-N-[2-Chloro-4-(phenyl-sulphonyl)phenyl]-2-hydroxy-2-methyl-3,3,3-trifluoropropanamide | 1.6 (s, 3H), 7.6 (t, 2H), 7.68 (m, 1H), 7.9–8.05 (m, 4H), 8.13 (d, 1H), 8.27 (d, 1H), 9.9 (br s, 1H) | 406 (M − H)$^-$ | 10 |
| 20 | (R)-N-[2-Bromo-4-(phenyl-sulphonyl)phenyl]-2-hydroxy-2-methyl-3,3,3-trifluoropropanamide | 1.6 (s, 3H), 7.58–7.78 (m, 3H), 8.0 (m, 4H), 8.2 (d, 1H), 8.3 (d, 1H), 9.85 (s, 1H) | 452 (M − H)$^-$ | 16 |
| 21 | (R)-N-[2-Chloro-4-(4-fluorophenylsulphonyl)phenyl)-2-hydroxy-2-methyl-3,3,3-trifluoropropanamide | 1.6 (s, 3H), 7.46 (t, 2H), 8.0 (dd, 1H), 8.08 (m, 2H), 8.15 (d, 1H), 8.3 (d, 1H), 9.85 (br s, 1H) | 426 (M + H)$^+$ | 11c |
| 22 | N-[2-Chloro-4-(phenyl-sulphonyl)phenyl]-2-hydroxy-2-trifluoromethylbutanamide | 0.87 (t, 3H), 1.8 (m, 1H), 2.1 (m, 1H), 7.62 (m, 3H), 7.9 (br s, 1H), 7.98 (m, 3H), 8.1 (s, 1H), 8.25 (d, 1H), 9.8 (br s, 1H) | 420 (M − H)$^-$ | 10a |
| 23 | N-[2-Chloro-4-(phenyl-sulphonyl)phenyl]-3,3-difluoro-2-hydroxy-2-methyl-propanamide | 1.4 (s, 3H), 6.1 (t, 1H), 7.2 (s, 1H), 7.62 (m, 3H), 7.98 (m, 3H), 8.1 (d, 1H), 8.4 (d, 1H), 9.79 (s, 1H) | 388 (M − H)$^-$ | 23 |
| 24 | N-[2-Chloro-4-(phenyl-sulphonyl)phenyl]-(1-hydroxy-1-cyclopropyl)carboxamide | 1.02 (m, 2H), 1.2 (m, 2H), 7.02 (s, 1H), 7.6,(m, 3H), 8.0 (m, 3H), 8.12 (s, 1H), 8.3 (d,1H), 9.75 (s, 1H) | 350 (M − H)$^-$ | 24 |
| 25 | N-[2-Chloro-4-(phenyl-sulphonyl)phenyl]-2-hydroxy-2-methylbutanamide | 0.8 (t, 3H), 1.3 (s, 3H), 1.57 (m, 1H), 1.72 (m, 1H), 6.06 (s, 1H), 7.6 (m, 3H), 7.95 (m, 3H), 8.08 (s, 1H), 8.55 (d, 1H), 9.8 (s, 1H) | 366 (M − H)$^-$ | 25 |
| 26 | N-[2-Chloro-4-(phenyl-sulphonyl)phenyl]-2-ethyl-2-hydroxybutanamide | 0.8 (t, 6H), 1.55 (m, 2H), 1.75 (m, 2H), 5.81 (s, 1H), 7.62 (m, 3H), 7.95 (m, 3H), 8.08 (d, 1H), 8.53 (d, 1H), 9.75 (s, 1H) | 380 (M − H)$^-$ | 26 |
| 27 | (R)-N-[2-Fluoro-4-(2-fluoro-phenylsulphinyl)phenyl]-2-hydroxy-2-methyl-3,3,3-trifluoropropanamide | (CDCl$_3$): 1.75 (s, 3H), 4.27 (br d, 1H), 7.08 (t, 1H), 7.35 (t, 1H), 7.45 (m, 1H), 7.6 (m, 1H), 7.75 (s, 1H), 7.88 (t, 1H), 8.54 (m, 1H), 9.2 (s, 1H) | 408 (M − H)$^-$ | 20e |
| 28[2] | (R)-N-[2-Chloro-4-(thien-2-yl-sulphonyl)phenyl]-2-hydroxy-2-methyl-3,3,3-trifluoropropanamide | (CDCl$_3$): 1.75 (s, 3H), 3.50 (s, 1H), 7.10 (t, 1H), 7.70 (m, 2H), 7.90 (m, 1H), 8.05 (s, 1H), 8.60 (d, 1H), 9.25 (br s, 1H) | 414 (M + H)$^+$ | 11a |
| 29 | (R)-N-[2-Chloro-4-(3-methoxy phenylsulphonyl)phenyl]-2-hydroxy 2-methyl-3,3,3-trifluoropropanamide | (CDCl$_3$): 1.7 (s, 3H), 3.56 (s, 1H), 3.82 (s, 3H), 7.07 (m, 1H), 7.36–7.49 (m, 3H), 7.83 (dd, 1H), 7.79 (d, 1H), 8.58 (d, 1H), 9.23 (br s, 1H) | 436 (M − H)$^-$ | 11b |
| 30 | (R)-N-[2-Chloro-4-(4-bromo-phenylsulphinyl)phenyl)-2 hydroxy-2-methyl-3,3,3-trifluoropropanamide | (CDCl$_3$): 1.68 (s, 3H), 3.9 and 3.98 (2 × s, 1H), 7.4 (d, 3H), 7.57 (d, 2H), 7.63 (d, 1H), 8.48 (m, 1H), 9.09 and 9.1 (2 × br s, 1H). | 468 (M − H)$^-$ | 11d |
| 31[3] | (R)-N-[2-Chloro-4-(2-trifluoro-methylphenylsulphonyl) phenyl]-2-hydroxy-2-methyl-3,3,3-trifluoropropanamide | (CDCl$_3$): 1.75 (s, 3H), 3.95 (br s, 1H), 7.70–7.95 (m, 5H), 8.40 (d, 1H), 8.60 (d, 1H), 9.35 (br s, 1H) | 474 (M − H)$^-$ | 27e |
| 32 | (R)-N-[2-Chloro-4-trifluoro-methylphenylsulphonyl) phenyl]-2-hydroxy-2-methyl-3,3,3-trifluoropropanamide | (CDCl$_3$): 1.75 (s, 3H), 3.60 (br s, 1H), 7.75 (d, 2H), 7.85 (dd, 1H), 8.00 (d, 1H), 8.05 (d, 2H), 8.75 (d, 1H), 9.35 (br s, 1H) | 474 (M − H)$^-$ | 27f |

-continued

| EX | COMPOUND | NMR | MS | Meth |
|---|---|---|---|---|
| 33 | (R)-N-[2-Chloro-4-(3-trifluoro-methylphenylsulphonyl)phenyl]-2-hydroxy-2-methyl-3,3,3-trifluoropropanamide | (CDCl$_3$): 1.75 (s, 3H), 3.55 (br s, 1H), 7.75 (t, 1H), 7.85 (td, 2H), 8.05 (dd, 1H), 8.15 (d, 1H), 8.20 (s, 1H), 8.85 (d, 1H), 9.30 (bs, 1H) | 474 (M − H)$^-$ | 27g |

[1]Optical purity: 97.8% ee by chiral HPLC (Chiralcel OJ column, 10% ethanol/hexane, flow rate: 1 ml/minute).
[2]Product was purified by chromatography eluting with 10–20% ethyl acetate/hexane.
[3]Product was purified by chromatography eluting with 20–66% ether/hexane.

Example 34

(R)-N-[2-Fluoro-4-(phenylsulphinyl)phenyl]-2-hydroxy-2-methyl-3,3,3-trifluoropropanamide m-Chloroperbenzoic acid (55%, 0.157 g) was added to a solution of (R)-N-[2-fluoro-4-(phenylthio)phenyl]2-hydroxy-2-methyl-3,3,3-trifluoropropanamide (Method 7) (0.212 g) in dichloromethane (5 ml) and the mixture was stirred at ambient temperature for 90 minutes. Ether (20 ml) was added and the solution was washed with saturated aqueous sodium carbonate solution (2×10 ml) and brine then dried. Volatile material was removed by evaporation and the residue was purified by chromatography on a silica gel Mega Bond Elut column eluting with 20–30% ethyl acetate/hexane to give the title compound (0.138 g) as a gum. NMR: 1.55 (s, 3H), 7.5–7.6 (m, 4H), 7.66 (d, 1H), 7.74 (m, 2H), 7.87 (t, 1H), 9.8 (br s, 1H); MS: 374 (M−H)$^-$.

Examples 35–39

Following the procedure of Example 34 and using the appropriate starting material the following compound was prepared. "Meth" relates to the method used to make the starting materials (see below).

Example 40

(R)-N-[4-(4-Bromophenylsulphonyl)-2-chlorophenyl]-2-hydroxy-2-methyl-3,3,3-trifluoropropanamide Oxalyl chloride (0.029 ml) was added to a stirred suspension of (R)-(+)-2-hydroxy-2-methyl-3,3,3-trifluoropropanoic acid (Method 9) (0.047 g) in dichloromethane (3 ml) containing DMF (1 drop). The mixture was stirred at ambient temperature for 30 minutes and was then added to a solution of 4-(4-bromophenylsulphonyl)-2-chloroaniline (Method 12) (0.104 g) in dichloromethane (3 ml) and stirred a further 1 hour. Water (10 ml) was added and the mixture was extracted with dichloromethane (3×20 ml). The organic extracts were combined, washed with brine then dried. Volatile material was removed by evaporation and the residue was purified by flash chromatography on silica gel eluting with 1% methanol/dichloromethane to give the title compound (0.049 g) as a foam. NMR (CDCl$_3$): 1.78 (s, 3H), 7.65 (d, 2H), 7.8 (m, 3H), 8.0 (s, 1H), 8.6 (d, 2H), 9.3 (s, 1H); MS: 485 (M$^+$).

Example 41

Following the procedure of Example 40 and using the appropriate starting material (p-thiocresole) the following compound was prepared.

| EX | COMPOUND | NMR | MS | Meth |
|---|---|---|---|---|
| 35 | (R)-N-[2-Chloro-4-(phenyl-sulphinyl)phenyl]-2-hydroxy-2-methyl-3,3,3-trifluoro-propanamide | 1.6 (s, 3H), 7.5 (m, 3H), 7.7 (m, 3H), 7.8 (s, 2H), 8.1 (d, 1H), 9.8 (s, 1H) | 390 (M − H)$^-$ | 10 |
| 36[1,3] | (R)-N-[2-Chloro-4-(2-nitro-phenylsulphonyl)phenyl]-2-hydroxy-2-methyl-3,3,3-trifluoropropanamide | 1.6 (s, 3H), 8.0 (m, 5H), 8.05 (s, 1H), 8.4 (m, 2H), 9.9 (s, 1H) | 451 (M − H)$^-$ | 27 |
| 37 | (R)-N-[2-Chloro-4-(4-nitro-phenylsulphonyl)phenyl]-2-hydroxy-2-methyl-3,3,3-trifluoropropanamide | (CDCl$_3$): 1.65 (s, 3H), 7.8 (d, 1H), 7.9 (s,1H), 8.0 (d, 2H), 8.3(d, 2H), 8.6 (d, 2H), 9.3 (s, 1H) | 451 (M − H)$^-$ | 27a |
| 38[1,3] | (R)-N-[2-Chloro-4-(3-nitro-phenylsulphonyl)phenyl]-2-hydroxy-2-methyl-3,3,3-trifluoropropanamide | (CDCl$_3$): 2.75 (s, 3H), 3.55 (s, 1H), 7.75 (t, 1H), 7.90 (dd, 1H), 8.10 (s, 1H), 8.25 (d, 1H), 8.45 (d, 1H), 8.70 (d, 1H), 8.75 (s, 1H), 9.30 (br s, 1H) | 451 (M − NH$_4$)$^-$ | 30 |
| 39 | (R)-N-[2-Chloro-4-(4-fluoro-phenylsulphinyl)phenyl]-2-hydroxy-2-methyl-3,3,3-trifluoropropanamide | (CDCl$_3$): 1.74 (s, 3H), 4.16 and 4.24 (2 × br s, 1H), 7.19 (t, 2H), 7.49 (d, 1H), 7.63 (dd, 2H), 7.7 (d, 1H), 8.52 (m, 1H), 9.2 (br s, 1H) | 408 (M − H)$^-$ | 20c |

[1]Product was purified by chromatography on a silica gel Mega Bond Elut column, eluting with 5–60% ethyl acetate/hexane.

| EX | COMPOUND | NMR (CDCl$_3$) | MS |
|---|---|---|---|
| 41 | (R)-N-[2-Chloro-4-(4-methylphenyl-sulphonyl)phenyl]-2-hydroxy-2-methyl-3,3,3-trifluoropropanamide | 1.75 (s, 3H), 2.4 (s, 3H), 7.3 (d, 2H), 7.8 (m, 3H), 8.0 (s, 1H), 8.6 (d, 2H), 9.25 (s, 1H) | 420 (M − H)$^-$ |

Example 42

(R)-N-[2-Chloro-4-(2-methoxyphenylsulphonyl)phenyl]-2-hydroxy-2-methyl-3,3,3-trifluoropropanamide m-Chloroperbenzoic acid (55%, 0.424 g) was added to a solution of (R)-N-[2-chloro-4-(2-methoxyphenylthio)phenyl]-2-hydroxy-2-methyl-3,3,3-trifluoropropanamide (Method 19) (0.166 g) in dichloromethane (10 ml) and the mixture was red at ambient temperature for 18 hours. The mixture was then washed with saturated aqueous sodium hydrogen carbonate solution (3×70 ml), water (50 ml) and brine then dried. tile material was removed by evaporation to give the title compound (0.137 g) as a solid. 82–84° C.; NMR (CDCl$_3$): 1.75 (s, 3H), 3.80 (s, 3H), 6.90 (d, 1H), 7.10 (m, 1H), 7.55 (m, 1H), 7.90 (dd, 1H), 8.05 (d, 1H), 8.10 (dd, 1H), 8.60 (d, 1H), 9.35 (br s, 1H); MS: 436 (M−H)$^-$; EA: C$_{17}$H$_{15}$ClF$_3$NO$_5$S.0.17 CH$_2$Cl$_2$ requires C, 46.1; H, 3.4; N, 3.1%; found: C, 46.0; N, 3.5; N, 3.1%.

Examples 43–47

Following the procedure of Example 42 and using the appropriate starting material the following compounds were prepared. "Meth" relates to the method used to make the starting materials (see below).

Example 48

(R)-2-Hydroxy-N-[2-methoxy-4-(phenylsulphonyl)phenyl]-2-methyl-3,3,3-trifluoropropanoic Oxalyl chloride (0.044 ml) was added to a stirred suspension of (R)-(+)-2-hydroxy-2-methyl-3,3,3-trifluoropropanoic acid (Method 9) (0.081 g) in dichloromethane (2 ml) containing DMF (1 drop). The mixture was stirred at ambient temperature for 2 hours and was then added to a solution of 2-methoxy-4-phenylsulphonylaniline (Method 21) (0.107 g) and 2,6di-tert-butylpyridine (0.12 ml) in dichloromethane (2 ml) and stirred a further 5 hours. Hexane (1 ml) was added and the solution was transferred to a silica gel Mega Bond Elut column and eluted with 30–40% ethyl acetate/hexane to give the title compound (0.070 g) as a foam. NMR: 1.55 (s, 3H), 3.97 (s, 3H), 7.5–7.7 (m, 5H), 7.9–8.0 (m, 3H), 8.4 (d, 1H), 9.62 (s, 1H); MS: 402 (M−H)$^-$.

Examples 49–52

Following the procedure of Example 48 and using racemic 2-hydroxy-2-methyl-3,3,3-trifluoropropanoic acid and the appropriate aniline the following compounds were prepared.

| EX | COMPOUND | NMR (CDCl$_3$) | MS | Meth |
|---|---|---|---|---|
| 43 | R)-N-[2-Chloro-4-(4-methoxy-phenylsulphonyl)phenyl]-2-hydroxy-2-methyl-3,3,3-trifluoro-propanamide | 1.75 (s, 3H), 3.85 (s, 3H), 7.00 (d, 2H), 7.85 (dd, 1H), 7.90 (d, 2H), 7.95 (d, 1H), 8.60 (d, 1H), 9.20 (br s, 1H) | 436 (M − H)$^-$ | 20a |
| 44 | (R)-N-[2-Chloro-4-(2-fluorophenyl-sulphonyl)phenyl]-2-hydroxy-2-methyl-3,3,3-trifluoropropanamide | 1.75 (s, 3H), 3.65 (br s, 1H), 7.15 (t, 1H), 7.35 (t, 1H), 7.60 (m, 1H), 7.95 (d, 1H), 8.10 (m, 2H), 8.60 (d, 1H), 9.30 (br s, 1H) | 424 (M − H)$^-$ | 20b |
| 45 | (R)-N-[2-Chloro-4-(3-fluorophenyl-sulphonyl)phenyl]-2-hydroxy-2-methyl-3,3,3-trifluoropropanamide | 1.75 (s, 3H), 3.61 (s, 1H), 7.3 (m, 1H), 7.5 (m, 1H), 7.6 (d, 1H), 7.73 (d, 1H), 7.86 (m, 1H), 8.0 (d, 1H), 8.62 (d, 1H), 9.15 (br s, 1H) | 424 (M − H)$^-$ | 20d |
| 46 | (R)-N-[2-Fluoro-4-(2-fluorophenyl-sulphonyl)phenyl]-2-hydroxy-2-methyl-3,3,3-trifluoropropanamide | 1.59 (s, 3H), 7.38–7.55 (m, 2H), 7.7–7.9 (m, 4H), 8.05 (q, 2H), 9.85 (br s, 1H) | 408 (M − H)$^-$ | 20e |
| 47 | (R)-N-[2-Chloro-4-((2-methylfuran-3-yl)sulphonyl)phenyl]-2-hydroxy-2-methyl-3,3,3-trifluoro-propanamide | 1.75 (s, 3H), 2.55 (s, 3H), 3.6 (s, 1H), 6.55 (dd, 1H), 7.25 (dd, 1H), 7.8 (dd, 1H), 7.95 (d, 1H), 8.6 (d, 1H), 9.25 (br s, 1H) | 410 (M − H)$^-$ | 27l |

| EX | COMPOUND | NMR | MS |
|---|---|---|---|
| 49[1] | N-(2-Bromo-4-trifluoromethoxy-phenyl)-2-hydroxy-2-methyl-3,3,3-trifluoropropanamide | 1.6 (s, 3H), 7.45 (d, 1H), 7.8 (s, 1H), 7.81 (br s, 1H), 8.03 (d, 1H), 9.8 (br s, 1H) | 394, 396 $(M - H)^-$ |
| 50[1] | N-(2-Bromo-4-trifluoromethyl-phenyl)-2-hydroxy-2-methyl-3,3,3-trifluoropropanamide | 1.6 (s, 3H), 7.8 (dd, 1H), 8.0 (br s, 1H), 8.1 (d, 1H), 8.3 (d, 1H), 9.9 (br s, 1H) | 378, 380 $(M - H)^-$ |
| 51[1] | N-(2-Chloro-4-trifluoromethyl-phenyl)-2-hydroxy-2-methyl-3,3,3-trifluoropropanamide | 1.6 (s, 3H), 7.78 (d, 1H), 7.96 (br s, 1H), 7.98 (s, 1H), 8.15 (d, 1H), 9.85 (br s, 1H) | 334 $(M - H)^-$ |
| 52[1] | N-(2-Chloro-4-cyanophenyl)-2-hydroxy-2-methyl-3,3,3-trifluoropropanamide | 1.6 (s, 3H), 7.85 (dd, 1H), 8.0 (s, 1H), 8.18 (d, 1H), 8.25 (d, 1H), 9.9 (br s, 1H); | 291, 293 $(M - H)^-$ |

[1]No 2,6-di-tert-butylpyridine was used and the reaction mixture was filtered before treating with hexane.

Example 53

3-Hydroxy-3-methyl-1-(4-phenylsulphonyl-2-fluorophenyl)-4,4,4-trifluorobut-1-yne s-Butyllithium (0.24 ml of a 1.3M solution in hexanes) was added dropwise to a solution of 4-phenylsulphonyl-2-fluorophenylethyne (Method 28) (0.08 g) in dry THF (3 ml) at −50° C. After 25 minutes a solution of 1,1,1-trifluoroacetone (0.035 g) in dry THF (0.5 ml) was added and the mixture was allowed to warm to ambient temperature overnight. Water (10 ml) was added and THF was evaporated off under reduced pressure. The residue was diluted with water (30 ml) and extracted with ethyl acetate (30 ml). The organic layer was washed with brine then dried. Volatile material was removed by evaporation and the residue was purified by chromatography on a silica gel Mega Bond Elut column eluting with 0–30% ethyl acetate/hexane then triturated with hexane to give the title compound (0.038 g) as a solid. NMR (CDCl$_3$): 1.75 (s, 3H), 2.75 (s, 1H), 7.5–7.75 (m, 6H), 7.93 (d, 2H); EA: C$_{17}$H$_{12}$F$_4$O$_3$S requires C, 54.8; H, 3.3%; found: C, 54.4; H, 3.4%.

Examples 54

Following the procedure of Example 53 and using the appropriate starting material the following compound was prepared.

| EX | COMPOUND | NMR (CDCl$_3$) | MS |
|---|---|---|---|
| 54[1] | 3-Hydroxy-1-(4-phenylsulphonyl-2-fluorophenyl)-3-trifluoromethyl-4,4,4-trifluorobut-1-yne | 4.0 (br s), 7.5–7.75 (m, 6H), 7.94 (d, 2H) | 426 (M$^+$) |

Examples 55–60

Following the procedure of Method 3 (see below) and using the appropriate starting material to replace the 6-nitro-3-(4-pyridylthio)anisole the following compounds were prepared. "Meth" relates to the method used to make the starting materials (see below).

| EX | COMPOUND | NMR | MS | Meth |
|---|---|---|---|---|
| 55 | (R)-N-[2-Chloro-4-(pyrimid-2-yl-sulphonyl)phenyl]-2-hydroxy-2-methyl-3,3,3-trifluoropropanamide | 1.64 (s, 3H), 7.82 (t, 1H), 8.01 (dd, 1H), 8.1 (br s, 1H), 8.13 (d, 1H), 8.4 (d, 1H), 9.05 (d, 2H), 9.94 (br s, 1H) | 408 $(M - H)^-$ | 27b |
| 56 | (R)-N-[2-Chloro-4-(pyrid-4-ylsulphonyl)phenyl]-2-hydroxy-2-methyl-3,3,3-trifluoropropanamide | (CDCl$_3$ + d$_6$-DMSO): 1.59 (s, 3H), 7.5 (br s, 1H), 7.7 (dd, 2H), 7.8 (dd, 1H), 7.91 (d, 1H), 8.6 (d, 1H), 8.76 (dd, 2H), 9.75 (br s, 1H) | 407 $(M - H)^-$ | 8c |
| 57[1] | (R)-N-[2-(5-Methyl-thien-2-ylsulphonyl)phenyl]-2-hydroxy-2-methyl-3,3,3-trifluoropropanamide | (CDCl$_3$): 1.75 (s, 3H), 2.50 (s, 3H), 3.50 (br s, 1H), 6.75 (m, 1H), 7.50 (m, 1H), 7.85 (dd, 1H), 8.00 (d, 1H), 8.60 (d, 1H), 9.20 (br s, 1H) | 428 $(M + H)^+$ | 27h |
| 58 | (R)-N-[2-Chloro-4-(imidazol-2-ylsulphonyl)phenyl]-2-hydroxy-2-methyl-3,3,3-trifluoropropanamide | 1.62 (s, 3H), 7.35 (br s, 2H), 7.95 (dd, 1H), 8.07 (d, 1H), 8.32 (d, 1H), 9.95 (br s, 1H), 13.9 (br s, 1H) | 396 $(M - H)^-$ | 27i |
| 59 | (R)-N-[2-Chloro-4-(pyrid-2-ylsulphonyl)phenyl]-2-hydroxy-2-methyl-3,3,3-trifluoropropanamide | 1.6 (s, 3H), 7.72 (m, 1H), 8.0 (dd, 1H), 8.07 (br s, 1H), 8.1 (d, 1H), 8.17 (m, 1H), 8.24 (d, 1H), 8.33 (d, 1H), 8.7 (m, 1H), 9.95 (br s, 1H) | 407 $(M - H)^-$ | 27j |
| 60 | (R)-N-[2-Chloro-4-(pyrid-3-ylsulphonyl)phenyl]-2-hydroxy-2-methyl-3,3,3-trifluoropropanamide | 1.6 (s, 3H), 7.66 (m, 1H), 8.05 (dd, 2H, including br s for OH), 8.26 (d, 1H), 8.34 (d, 1H), 8.42 (m, 1H), 8.87 (m, 1H), 9.2 (d, 1H), 9.94 (br s, 1H) | 407 $(M - H)^-$ | 27k |

[1]Product was purified by chromatography eluting with 10–100% ethyl acetate/hexane

Example 61

(R)-N-[2-Chloro-4-(thiazol-2-ylsulphonyl)phenyl]-2-hydroxy-2-methyl-3,33-trifluoropropanamide A solution of Oxone (Trademark of E. I. du Pont de Nemours & Co., Inc., potassium peroxymonosulphate) (0.317 g) in a 1M solution of sodium acetate (2 ml) was added to a stirred solution of (R)-N-[2-chloro-4-(2-thiazolylthio)phenyl]-2-hydroxy-2-methyl-3,3,3-trifluoropropanamide (Method 27c) (0.131 g) in methanol (4 ml). After 2 hours water (40 ml) was added and the mixture was extracted with ethyl acetate (2×50 ml). The reaction was repeated on the same scale and the organic extracts were combined and concentrated by evaporation to give a foam. This material was purified by chromatography on silica gel eluting with 7.5–10% ether/dichloromethane to give the title compound (0.119 g) as a solid. NMR: 1.6 (s, 3H), 8.05 (dd, 1H), 8.1 (br s, 1H), 8.12 (m, 2H), 8.3 (d, 1H), 8.4 (d, 1H), 9.9 (br s, 1H); MS: 413 (M−H)$^{31}$; EA: $C_{13}H_{10}ClF_3N_2O_4S_2$ requires C, 37.6; H, 2.4; N, 6.8%; found C, 37.5; H, 2.2; N, 6.4%.

Preparation of Starting Materials

The starting materials for the Examples above are either commercially available or are readily prepared by standard methods from known materials. For example the following reactions (Methods 1–32) are illustrations but not limitations of the preparation of some of the starting materials used in the above reactions.

Method 1
4-Amino-3-fluorobenzophenone

To stirred polyphosphoric acid (125 g) at 90° C. was added benzoic acid (18.32 g) and 2-fluoroaniline (8.33 g) and the bath temperature was raised to 200° C. for 1 hour. The heating bath was removed and the stirred mixture was treated cautiously with water (60 ml). The mixture was stirred at 140–160° C. for 1 hour, the heating bath was removed, and 3M hydrochloric acid was added (50 ml). The mixture was poured into water (750 ml) and filtered through diatomaceous earth with a dichloromethane wash. The filtrate was made basic with 15% sodium hydroxide and the mixture was again filtered through diatomaceous earth with a dichloromethane wash. The combined dichloromethane extracts were washed (saturated aqueous sodium hydrogen carbonate), dried, filtered, and evaporated. Chromatography, with ether/hexanes (gradient, 10/90 to 50/50) as the eluent, followed by recrystallization from hexanes, yielded the title compound as a light yellow solid (7.48 g). M.p. 83–85° C.; MS: 216 (M+H); NMR (400 MHz): 6.27 (brs, 2H), 6.80 (t, 1H, J=8.6), 7.36 (q, 1H, J=8.4, 1.9), 7.41 (q, 1H, J=12.4, 1.9), 7.49–7.51 (m, 2H) 7.60–7.63 (m, 3H); EA: $C_{13}H_{10}FNO$ requires C, 72.55; H, 4.68; N, 6.51%; found: C, 72.51; H, 4.82; N, 6.42%.

Method 2
2-Methoxy-4-(pyrid-4-ylsulphonyl)aniline

To a stirred slurry of 6-nitro-3-(pyrid-4-yl)sulphonyl) anisole (Method 3) (3.40 g) and absolute ethanol (30 ml) was added stannous chloride dihydrate (13.0 g) in one portion. The mixture was heated at reflux for 50 minutes, poured onto ice-water (200 ml) and made basic with aqueous 15% sodium hydroxide. The mixture was extracted with ethyl acetate and the organics were evaporated to yield a white solid which was recrystallized from boiling absolute ethanol. After cooling the solid was filtered to yield the title compound as a white solid (2.42 g). M.p. 163–165° C.; MS: 265(M+H); NMR: 3.85 (s, 3H), 6.01 (s, 2H), 6.73 (d, 1H, J=8.4), 7.23 (d, 1H, J=2.0), 7.34 (dd, 1H, J=2.0, 8.4), 7.81–7.83 (m, 2H), 8.80–8.82 (m, 2H); EA: $C_{12}H_{12}N_2O_3S$ requires C, 54.53; H, 4.58; N, 10.60%; Found: C, 54.45; H, 4.54; N, 10.58%.

Method 3
6-Nitro-3-(pyrid-4-ylsulphonyl)anisole

To a stirred solution of 6-nitro-3-(pyrid-4-ylthio)anisole (Method 4) (6.49 g) and acetic acid (200 ml) was rapidly added a solution of potassium permanganate (4.69 g) in water (100 ml). After stirring for 1 hour, the mixture was clarified by the addition of solid sodium sulphite, diluted to a volume of 1 liter with water and the resulting solid was collected. Recrystallization from absolute ethanol (300 ml) yielded the title compound (3.43 g). M.p. 123–124° C.; NMR: 4.07 (s, 3H), 7.75 (dd, 1H, J=1.7, 8.4), 7.90 (d, 1H, J=1.7), 8.02–8.04 (m, 2H), 8.12 (d, 1H, J=8.4), 8.92–8.94 (m, 2H); EA: $C_{12}H_{10}N_2O_5S$ requires C, 48.98; H,3.42; N, 9.52%; found: C, 48.81; H, 3.45; N, 10.02%.

Method 4
6-Nitro-3-(pyrid-4-ylthio)anisole

5-Chloro-2-nitroanisole (9.38 g) was added to a solution of 4-mercaptopyridine potassium salt prepared by adding 4-mercaptopyridine (6.67 g) to a solution of potassium hydroxide (3.37 g) in methanol (30 ml) followed by evaporation of the methanol) and DMF (40 ml). After stirring for 1 hour, the mixture was heated at 110° C. for 4 hours and allowed to stand overnight. The reaction mixture was poured into ice-water (1 liter), stirred for 15 minutes, and the yellow solid was filtered off. The solid was stirred with 3M hydrochloric acid (800 ml) for 1 hour, filtered, and the filter cake was washed with 3M hydrochloric acid then water. The filtrate was cooled in an ice-bath and made basic with 28% aqueous ammonium hydroxide to yield approximately 2 g of the title compound. The filter cake was suspended in water (100 ml) with stirring and the mixture was made basic with saturated sodium hydrogen carbonate and extracted with ethyl acetate. The organics were combined, dried, filtered and evaporated to give a yellow solid that was triturated with hexane and filtered to give additional title compound (total yield 6.49 g). M.p. 97–100° C.; MS: 263 (M+H); NMR: 3.94 (s, 3H), 7.17 (dd, 1H, J=1.8, 8.4), 7.27–7.7.29 (m, 2H), 7.51 (d, 1H, J=1.8), 7.97 (d, 1H, J=8.4), 8.48–8.50 (m, 2H).

Method 5
4-Amino-3-cyanobenzophenone

To a stirred refluxing mixture of 3-cyano-4-nitrobenzophenone (Method 6) (1.50 g) and iron powder (3.64 g) in ethanol (50 ml) was added dropwise over 0.5 hour a solution of concentrated hydrochloric acid (0.35 ml) in ethanol (14 ml) and reflux was maintained overnight. The hot mixture was filtered through diatomaceous earth and the reaction flask and diatomaceous earth pad was washed with three 50 ml portions of ethanol. The combined filtrate was evaporated to yield a tan solid. Chromatography (eluent 10% to 40% ethyl acetate gradient in dichloromethane) gave the title compound (0.21 g) as a tan solid. M.p. 158–160° C.;
EA: $C_{14}H_{10}N_2O.0.25H_2O$ requires C, 74.35; H, 4.33; N, 12.32%; found: C, 74.16; H, 4.66; N, 12.35%.

Method 6
3-Cyano-4-nitrobenzophenone

A stirred mixture of 3-chloro-4-nitrobenzophenone (5.00 g), (J. Org. Chem., 1962, 27, 1605–1608), and copper(I) cyanide (2.57 g) in DMF (50 ml) was heated at reflux for 16 hours. The hot reaction mixture was then poured into a stirred solution of ferric chloride (15.30 g) concentrated hydrochloric acid (5 ml) and water (200 ml). The mixture was heated at 65–70° C. for 30 minutes, cooled to ambient temperature treated with ethyl acetate (250 ml) and stirred vigorously for 5 minutes. The organic phase was separated and the aqueous layer extracted with another 250 ml portion of ethyl acetate. The combined organics were dried, filtered and evaporated to give a brown oil. Chromatography (eluent toluene) gave the title compound (2.77 g) as a yellow solid. M.p. 117–119° C.; EA $C_{14}H_8N_2O_3$ requires C, 66.67; H, 3.02; N, 11.11%; found: C, 66.83; H, 2.99; N, 11.12%.

Method 7
(R)-N-[2-Fluoro-4-(phenylthio)phenyl]-2-hydroxy-2-methyl-3,33-trifluoropropanamide Oxalyl chloride (0.1 17 ml) was added to a stirred suspension of (R)-(+)-2-hydroxy-2-methyl-3,3,3-trifluoropropanoic acid (Method 9) (0.1 98 g) in dichloromethane (3.5 ml) containing DMF (1 drop). The mixture was stirred at ambient temperature for 2 hours and was then added to a solution of 2-fluoro-4-phenylthioaniline (Method 8) (0.219 g) in dichloromethane (5 ml) and stirred a further 2 hours. Ether (50 ml) was added and the mixture was washed with water (2×50 ml) and brine then dried. Volatile material was removed by evaporation to give the title compound (0.423 g) as a liquid that was used without further purification. NMR: 1.55 (s, 3H), 7.1 (d, 1H), 7.2 (m, 1H), 7.3–7.5 (m, 5H), 7.6 (s, 1H), 7.7 (t, 1H), 9.65 (s, 1H); MS: 358 (M−H)−.

Method 8
2-Fluoro-4-phenylthioaniline

Tetrakis(triphenylphosphine)palladium(0) (0.578 g) was added to a deoxygenated mixture of 2-fluoro-4-iodoaniline (2.37 g), thiophenol (1.07 ml) and sodium methoxide (1.13 g) in ethanol (80 ml). The mixture was further deoxygenated by evacuation and refilling with argon (3 cycles) then heated under reflux with stirring under argon for 18 hours, cooled and filtered. The filter was washed with ether (3×20 ml) and the filtrates were combined and volatile material was removed by evaporation. The residue was treated with dichloromethane (50 ml), filtered and reconcentrated. This crude product was purified by chromatography on a silica gel Mega Bond Elut column eluting with 50–70% dichloromethane/hexane to give the title compound (1.851 g) as a solid. M.p. 48–49° C.; NMR: 5.5 (s, 2H), 6.8 (t, 1H), 7.0–7.1 (m, 5H), 7.25 (t, 2H).

Methods 8a–8c

Using the procedure of Method 8 followed by the procedure of Method 7 the following compounds were prepared:

| Method | Replacement for thiophenol | Replacement for 2-fluoro-4-iodoaniline | Compound Prepared |
|---|---|---|---|
| 8a | o-thiocresol | 2-chloro-4-iodoaniline | (R)-N-[2-chloro-4-(2-methyl-phenylthio)phenyl]-2-hydroxy-2-methyl-3,3,3-trifluoropropanamide |
| 8b | — | 4-bromo-2-methylaniline | (R)-2-hydroxy-2-methyl-N-[2-methyl-4-(phenylthio)phenyl]-3,3,3-trifluoropropanamide |
| 8c[1] | 4-mercapto-pyridine | (R)-N-[2-chloro-4-iodo-phenyl]-2-hydroxy-2-methyl-3,3,3-trifluoro-propanamide | (R)-N-[2-chloro-4-(pyrid-4-ylthio)phenyl]-2-hydroxy-2-methyl-3,3,3-trifluoropropanamide |

[1]Method 8 only.

Method 9
(R)-(+)-2-Hydroxy-2-methyl-3,3,3-trifluoropropanoic acid

This compound was prepared by the method of Scheme 2 in World Patent Application Publication No. WO 9738124 for preparation of the (S)-(−) acid, i.e. Using the classical resolution method described in European Patent Application Publication No. EP 0524781, also for preparation of the (S)-(−) acid, except that (1S,2R)-norephedrine was used in place of (S)-(−)-1-phenylethylamine. The (R)-(+)-2-hydroxy-2-methyl-3,3,3-trifluoropropanoic acid thus obtained (in about 20% yield, of a maximum possible of 50%, after 3–5 recrystallization of the diastereomeric salt followed by liberation of the free acid by treatment with hydrochloric acid) was >98% enantiomerically pure based on NMR analysis of the (1S,2R)-norephedrine salt; $[\alpha]_D^{18}$=+18.1, c=8.8 in methanol.

Method 10
(R)-N-[2-Chloro-4-(phenylthio)phenyl]-2-hydroxy-2-methyl-3,3,3-trifluoropropanamide Oxalyl chloride (0.063 ml) was added to a stirred suspension of (R)-(+)-2-hydroxy-2-methyl-3,3,3-trifluoropropanoic acid (Method 9) (0.106 g) in dichloromethane (2 ml) containing DMF (1 drop). The mixture was stirred at ambient temperature for 90 minutes and was then added to a solution of 2-chloro-4-phenylthioaniline (Method 11) (0.143 g) in dichloromethane (4 ml) and stirred a further 3 hours. Ethyl acetate (30 ml) was added and the mixture was washed with water (2×30 ml) and brine then dried. Volatile material was removed by evaporation and the residue was purified by chromatography on a silica gel Mega Bond Elut column eluting with 15% ethyl acetate/hexane to give the title compound (0.153 g) as a gum. NMR: 1.57 (s, 3H), 7.26–7.41 (m, 6H), 7.44 (d, 1H), 7.82 (s, 1H), 7.95 (d, 1H), 9.74 (s, 1H); MS: 374 (M−H)−.

Method 10a

Using the procedure of Method 10, but using 2-hydroxy-2-trifluoromethylbutanoic acid as the starting material, the following compound was prepared.

| Method | Compound | NMR |
|---|---|---|
| 10a | N-[2-chloro-4-(phenylthio)phenyl]-2-hydroxy-2-trifluoromethyl-butanamide | 0.9 (t, 3H), 1.8 (m, 1H), 2.1 (m, 1H), 7.18 (m, 7H), 7.58 (br s, 1H), 7.92 (d, 1H), 9.65 (br s, 1H) |

Method 11
2-Chloro-4-phenylthioaniline

Tetrakis(triphenylphosphine)palladium(0) (0.1 15 g) was added to a deoxygenated mixture of 2-chloro-4-iodoaniline (0.507 g), thiophenol (0.214 ml) and sodium methoxide (0.227 g) in ethanol (20 ml). The mixture was further deoxygenated by evacuation and refilling with argon (3 cycles) then heated under reflux with stirring under argon for 18 hours, cooled, diluted with ether (30 ml) and filtered. Volatile material was removed by evaporation and the residue was purified by chromatography on a silica gel Mega Bond Elut column eluting with 10–15% ethyl acetate/hexane to give the title compound (0.443 g) as a solid. M.p. 59–60° C.; NMR: 5.78 (br s, 2H), 6.8 (t, 1H), 7.04 (m, 2H), 7.15 (m, 2H), 7.2–7.35 (m, 3H); EA: $C_{12}H_{10}ClNS$ requires C, 61.1; H, 4.3; N, 5.9; S, 13.6%; found: C, 60.8; H, 4.4; N, 5.7; S, 13.3%.

Methods 11a–d

Using the procedure of Method 11, but using the appropriate starting materials, the following compounds were prepared.

| Method | Compound | Replacement for thiophenol | Replacement for 2-chloro-4-iodoaniline |
|---|---|---|---|
| 11a[1] | (R)-N-[2-Chloro-4-(thien-2-ylthio)phenyl]-2-hydroxy-2-methyl-3,3,3-trifluoropropanamide | 2-mercaptothiophene | (R)-N-(2-chloro-4-iodophenyl)-2-hydroxy-2-methyl-3,3,3-trifluoropropanamide |
| 11b | (R)-N-[2-Chloro-4-(3-methoxyphenylthio)phenyl]-2-hydroxy-2-methyl-3,3,3-trifluoropropanamide | (R)-N-(2-chloro-4-mercaptophenyl)-2-hydroxy-2-methyl-3,3,3-trifluoropropanamide[2] | 3-iodoanisole |
| 11c[3] | (R)-N-[2-Chloro-4-(4-fluorophenylthio)phenyl]-2-hydroxy-2-methyl-3,3,3-trifluoropropanamide | 4-fluorobenzenethiol | (R)-N-[2-chloro-4-iodophenyl]-2-hydroxy-2-methyl-3,3,3-trifluoropropanamide |
| 11d[4] | (R)-N-[2-Chloro-4-(4-bromophenylthio)phenyl]-2-hydroxy-2-methyl-3,3,3-trifluoropropanamide | 4-bromobenzenethiol | (R)-N-[2-chloro-4-iodophenyl]-2-hydroxy-2-methyl-3,3,3-trifluoropropanamide |

[1]Product was purified by chromatography on silica gel eluting with 20–30% ethyl acetate/hexane.
[2]Method 31.
[3]Product contaminated with 2-chloro-4-(4-fluorophenylthio)aniline, removed after next step.
[4]Product impure.

Method 12
4-(4-Bromophenylsulphonyl)-2-chloroaniline

Iron powder (2.5 g) was added to a stirred mixture of 4-(4-bromophenylsulphonyl)-2-chloro-nitrobenzene (Method 13) (0.6 g), water (2 ml), concentrated hydrochloric acid (0.5 ml) and ethanol (10 ml). The mixture was heated under reflux for 1 hour then evaporated to near dryness and partitioned between ethyl acetate and water. The organic layer was separated, the aqueous layer was extracted with ethyl acetate (3×15 ml) and the organic extracts were combined and dried. Volatile material was removed by evaporation and the residue was purified by chromatography on a silica gel Mega Bond Elut column eluting with 0–25% ethyl acetate/hexane followed by trituration with ether to give the title compounde (0.11 g) as a solid. NMR: 6.42 (s, 2H), 6.82 (d, 1H), 7.5 (d, 1H), 7.8 (m, 5H); MS: 346 (M−H)−.

Method 13
4-(4-Bromophenylsulphonyl)-2-chloro-nitrobenzene

Hydrogen peroxide (0.9 ml of a 30 wt. % solution in water) was added to a solution of 4-(4-bromophenylthio)-2-chloro-nitrobenzene (Method 14) (0.635 g) in glacial acetic acid (4 ml) and the mixture was stirred and heated at 95° C. for 75 minutes then poured into water (15 ml) and extracted with ethyl acetate (3×10 ml). The organic extracts were combined, washed with brine and then dried. Volatile material was removed by evaporation and the residue was purified by chromatography on a silica gel Mega Bond Elut column eluting with 0–25% ethyl acetate/hexane to give the title compound (0.61 g). NMR: 7.9 (m, 2H), 8.0 (m, 2H), 8.1–8.3 (m, 2H), 8.4 (m, 1H).

Method 14
4-(4-Bromophenylthio)-2-chloro-nitrobenzene

A solution of 2-amino-4-(4-bromophenylthio) nitrobenzene (Method 15) (2.25 g) in warm glacial acetic acid (13 ml) was poured onto ice (20 ml). Concentrated hydrochloric acid (3.95 ml) was added and the mixture was stirred and cooled to <5° C. A solution of sodium nitrite (0.524 g) in water (5 ml) was added over 7 minutes and the mixture was stirred for 2 hours at 0–5° C. Aqueous sulphamic acid solution (10% w/v) was added until a negative starch iodide test was observed. Meanwhile toluene was added to a solution of cuprous chloride (0.745 g) in water (1 ml) and concentrated hydrochloric acid (1.15 ml) and the mixture was cooled to <0° C. The first preparation (diazonium salt) was then added to the cold cuprous chloride mixture over 5 minutes and the resultant mixture was stirred at ambient temperature for 18 hours. The organic layer was separated and the aqueous layer was extracted with toluene (3×10 ml). The organic extracts were combined, washed with water and brine then dried. Volatile material was removed by evaporation and the residue was purified by chromatography on a silica gel Mega Bond Elut column eluting with 0–15% ethyl acetate/hexane to give the title compound (0.644 g). MS: 343 (M+).

Method 15
2-Amino-4-(4-bromophenylthio)nitrobenzene

Sodium (0.269 g) was added to ethanol (20 ml) and the resultant solution was allowed to cool to ambient temperature then 4-bromothiophenol (2.21 g) was added. The mixture was stirred for 5 minutes then 5-chloro-2-nitroaniline (2 g) was added. The mixture was then heated under reflux under argon for 3 hours then allowed to cool down. The resultant solid was collected by filtration, washed with ethanol then dried to give the title compound (236 g) as a solid. NMR: 6.3 8 (dd, 1H), 6.65 (m, 1H), 7.42 (m, 4H), 7.7 (m, 2H), 7.9 (d, 1H); MS: 327 (M+H)+.

Method 15a

Using the procedure of Method 15 followed by the procedure of Methods 14, 13 and 12 the following compound was prepared:

| Method | Replacement for 4-bromothiophenol | Compound Prepared |
|---|---|---|
| 15a | p-Thiocresol | 4-(4-methylphenylsulphonyl)-2-chloroaniline |

Method 16
(R)-N-[2-Bromo-4-(phenylthio)phenyl]-2-hydroxy-2-methyl-3,3,3-trifluoropropanamide Oxalyl chloride (0.052 ml) was added to a stirred suspension of (R)-(+)-2-hydroxy-2-methyl-3,3,3-trifluoropropanoic acid (Method 9) (0.095 g) in dichloromethane (3 ml) containing DMF (1 drop). The mixture was stirred at ambient temperature for 2 hours and was then added to a solution of 2-bromo-4-phenylthioaniline (Method 17) (0.135 g) and 2,6-di-tert-butylpyridine (0.14 ml) in dichloromethane (5 ml) and stirred a further 3 hours. Volatile material was removed by evaporation and the residue was purified by chromatography on a silica gel Mega Bond Elut column eluting with 0–30% ethyl acetate/hexane to give the title compound (0.061 g) as a waxy solid. NMR: 1.59 (s, 3H), 7.25–7.50 (bm, 6H), 7.59 (s, 1H), 7.82 (bs, 1H), 7.98 (d,1H), 9.79 (s, 1H); MS: 420 (M−H)$^-$.

Method 17 s2-Bromo-4-phenylthioaniline

Iron powder (1.2 g) was added to a stirred mixture 2-bromo-4-phenylthionitrobenzene (Method 18) (0.6 g), water (1.6 ml), concentrated hydrochloric acid (0.4 ml) and ethanol (8 ml). The mixture was heated under reflux for 40 minutes then evaporated to near dryness and partitioned between ethyl acetate and water. The organic layer was separated, the aqueous layer was extracted with ethyl acetate (3×10 ml) and the organic extracts were combined and dried. Volatile material was removed by evaporation and the residue was purified by chromatography on a silica gel Mega Bond Elut column eluting with 0–35% ethyl acetate/hexane to give the title compound (0.145 g) as a waxy solid. NMR: 5.65 (s,2H), 6.8 (d, 1H), 7.05 (d, 2H), 7.1–7.3 (m, 4H), 7.42 (s, 1H); MS: 280 (M−H)$^-$.

Method 18

2-Bromo-4-phenylthionitrobenzene tert-Butyl nitrite (0.725 ml) was added to a slurry of copper(II)bromide (1.04 g) in acetonitrile (20 ml) at 0° C. 2-Amino-4-phenylthionitrobenzene (1 g, prepared as described in J. Med. Chem., 1975, 18, 1164) was added portionwise over 5 minutes and the mixture was stirred a further 2 hours at 0° C., allowed to warm to ambient temperature, and stirred a further 16 hours. Volatile material was removed by evaporation and the residue was purified by flash chromatography on silica gel eluting with 2% ethyl acetate/hexane to give the title compound (0.2 g) as an oil. NMR: 7.2 (d, 1H), 7.5–7.62 (m, 6H), 7.9 (d, 1H); MS: 311 (M$^+$).

Method 19

(R)-N-[2-Chloro-4-(2-methoxyphenylthio)phenyl]-2-hydroxy-2-methyl-3,3,3-trifluoropropanamide Tetrakis(triphenylphosphine)palladium(0) (0.03 g) was added to a deoxygenated mixture of (R)-N-[2-chloro-4-iodophenyl]-2-hydroxy-2-methyl-3,3,3-trifluoropropanamide (Method 20) (0.2 g), 2-methoxybenzenethiol (0.064 ml) and sodium methoxide (0.058 g) in ethanol (10 ml). The mixture was further deoxygenated by evacuation and refilling with argon (3 cycles) then heated under reflux with stirring under argon for 18 hours, treated with a further portion of tetrakis (triphenylphosphine)palladium(0) (0.03 g), heated a further 24 hours then cooled and filtered. Volatile material was removed by evaporation and the residue was purified by chromatography on a silica gel Mega Bond Elut column eluting with 0–10% ethyl acetate/hexane to give the title compound (0.166 g) as an oil. NMR (CDCl$_3$): 1.75 (s, 3H), 3.7 (br s, 1H), 3.85 (s, 3H), 6.9 (m, 2H), 7.2 (m, 1H), 7.3 (dd, 1H), 7.35 (m, 2H), 8.3 (d, 1H), 9.8 (br s, 1H); MS: 404 (M−H)$^-$.

Method 19a

Using the procedure of Method 19 the following compound was prepared:

| Meth | Replacement for (R)-N-[2-chloro-4-iodophenyl]-2-hydroxy-2-methyl-3,3,3-trifluoropropanamide | Replacement for 2-methoxy-benzenethiol | Compound Prepared |
| --- | --- | --- | --- |
| 19a[1] | 4-bromo-3-fluoro-iodobenzene | thiophenol | (4-bromo-3-fluoro-1-phenyl-thiobenzene) |

[1]Double the amount of palladium catalyst was used, and the compound was used without further purification.

Method 20

(R)-N-[2-Chloro-4-iodophenyl]-2-hydroxy-2-methyl-3,3,3-trifluoropropanamide

Oxalyl chloride (1.07 ml) was added dropwise to a stirred suspension of (R)-(+)-2-hydroxy-2-methyl-3,3,3-trifluoropropanoic acid (Method 9) (1.95 g) in dichloromethane (42 ml) and DMF (0.8 ml). The mixture was stirred at ambient temperature for 2 hours and was then added over 35 minutes to a solution of 2-chloro-4-iodoaniline (2.5 g) and 2,6-di-tert-butylpyridine (2.94 ml) in dichloromethane (40 ml) and stirred a further 18 hours. Volatile material was removed by evaporation and the residue was purified by flash chromatography on silica gel eluting with dichloromethane to give the title compound (2.85 g) as a solid. NMR: 1.6 (s, 3H), 7.7 (m, 2H), 7.8 (d, 1H), 7.9 (br s, 1H); MS: 392 (M−H)$^-$.

Methods 20a–20e

Using the procedure of Method 20 followed by the procedure of Method 19 the following compounds were prepared:

| Method | Replacement for 2-methoxybenzenethiol | Compound Prepared |
| --- | --- | --- |
| 20a | 4-Methoxybenzenethiol | R)-N-[2-chloro-4-(4-methoxyphenylthio)phenyl]-2-hydroxy-2-methyl-3,3,3-trifluoropropanamide |
| 20b | 2-Fluorothiophenol | (R)-N-[2-chloro-4-(2-fluorophenylthio)phenyl]-2-hydroxy-2-methyl-3,3,3-trifluoropropanamide |
| 20c | 4-Fluorothiophenol | (R)-N-[2-chloro-4-(4-fluorophenylthio)phenyl]-2-hydroxy-2-methyl-3,3,3-trifluoropropanamide |
| 20d | 3-Fluorothiophenol | (R)-N-[2-chloro-4-(3-fluorophenylthio)phenyl]-2-hydroxy-2-methyl-3,3,3-trifluoropropanamide |
| 20e[1] | 2-Fluorothiophenol | (R)-N-[2-fluoro-4-(2-fluorophenylthio)phenyl]-2-hydroxy-2-methyl-3,3,3-trifluoropropanamide |

[1]Double the amount of palladium catalyst was used for preparation of the starting material and 2-fluoro-4-iodoaniline was used in Method 20 in place of 2-chloro-4-iodoaniline.

Method 21

2-Methoxy-4-phenylsulphonylaniline

A solution of ammonium formate (0.1 83 g) in water (2.5 ml) was added to a mixture of 10% palladium on carbon (0.03 g) and 2-methoxy-4-phenylsulphonylnitrobenzene (Method 22) (0.213 g) in methanol (10 ml) and ethyl acetate (1 ml). The mixture was heated and stirred under reflux under argon for 4 hours then cooled and filtered through diatomaceous earth. The filter was washed with ethyl acetate (2×5 ml) and the filtrates were combined. The solution was concentrated by evaporation to approximately 2 ml and the resultant solid was collected, washed with water (2×5 ml) and dried in vacuo to give the title compound as a solid. M.p.149–150.5° C.; NMR: 3.8 (s, 3H), 5.78 (s, 2H), 6.67 (d, 1H), 7.17 (s, 1H), 7.26 (dd, 1H), 7.5–7.62 (m, 3H), 7.84 (d, 2H); MS: 262 (M–H)$^-$; EA: $C_{13}H_{13}NO_3S$ requires C, 59.3; H, 5.0; N, 5.3; S, 12.2%; found: C, 59.1; H, 4.9; N, 5.2; S, 12.2%.

Method 22

2-Methoxy-4-phenylsulphonylnitrobenzene

Hydrogen peroxide (0.4 ml of a 30 wt. % solution in water) was added to a solution of 2-methoxy-4-phenylthionitrobenzene (0.261 g) in glacial acetic acid (1.0 ml) and the mixture was stirred and heated at 100° C. for 2 hours. A few drops of water were added and the mixture was cooled and scratched to induce crystallisation. The resultant solid was collected, washed with water (2×5 ml) then dried in vacuo to give the title compound (0.263 g) as a solid. M.p. 128.5–129.5° C.; NMR: 4.01 (s, 3H), 7.67.7 (m, 3H), 7.73 (t, 1H), 7.81 (s, 1H), 8.05 ) apparent d, 3H); EA: $C_{13}H_{11}NO_5S$ requires C, 53.2; H, 3.8; N, 4.8; S, 10.9%; found: C, 52.9; H, 3.8; N, 4.6; S, 10.8%.

Methods 23–25

Using the procedure of Example 2 the following compounds were prepared.

| Method | Replacement for 2-hydroxy-2-methyl-3,3,3-triflu oropropanoic acid | Compound Prepared |
|---|---|---|
| 23 | 3,3-Difluoro-2-hydroxy-2-methyl propanoic acid[1] | N-[2-chloro-4-(phenylthio) phenyl]-3,3-difluoro-2-hydroxy-2-methylpropanamide |
| 24 | (1-Hydroxy-1-cyclopropyl) carboxylic acid | N-[2-chloro-4-(phenylthio) phenyl]-(1-hydroxy-1-cyclopropyl)carboxamide |
| 25 | 2-Hydroxy-2-methylbutanoic acid | N-[2-chloro-4-(phenylthio) phenyl]-2-hydroxy-2-methylbutanamide |

[1] Chemical Abstracts, 53:2078i 1959

Method 26

N-[2-Chloro-4-(phenylthio)phenyl]-2-ethyl-2-hydroxybutanamide

Acetyl chloride (0.785 g) was added dropwise to a stirred solution of 2-ethyl-2-hydroxybutanoic acid (0.528 g) in dry toluene (10 ml) whilst cooling in an ice/water bath. The mixture was heated at 80° C. for 2 hours then volatile material was removed by evaporation and thionyl chloride (0.595 g) was added to the residue. The resultant solution was heated at 80° C. for 2 hours then volatile material was removed by evaporation to give 2-acetoxy-2-ethylbutanoyl chloride (0.700 g). This material was dissolved in dry toluene then added slowly to a solution of 2-chloro-4-phenylthioaniline (Method 11) (0.235 g), and pyridine (0.336 g) in dry toluene (5 ml). The mixture was heated at 100° C. for 4 hours then dried. Volatile material was removed by evaporation and the residue was dissolved in methanol (15 ml) and lithium hydroxide monohydrate (0.200 g) was added. The mixture was stirred for 3 hours at ambient temperature then volatile material was removed by evaporation and the residue was partitioned between 2M aqueous hydrochloric acid and dichloromethane. The organic layer was dried and volatile material was removed by evaporation. The residue was purified by chromatography on a silica gel Mega Bond Elut column eluting with 5–10% ethyl acetate/hexane to give the title compound (0.19 g) as a gum. MS: 348 (M–H)$^-$.

Method 27

(R)-N-[2-Chloro-4-(2-nitrophenylthio)phenyl]-2-hydroxy-2-methyl-3,3,3-trifluoropropanamide A mixture of (R)-N-(2-chloro-4-mercaptophenyl)-2-hydroxy-2-methyl-3,3,3-trifluoropropanamide (0.1 g), 1-iodo-2-nitrobenzene (0.086 g), sodium methoxide (0.021 g), and cuprous chloride (0.014 g) in DMF (1 ml) was stirred and heated to 135° C. for 2.5 hours then allowed to cool to room temperature. The reaction mixture was diluted with water (5 ml) and poured onto a Varian Chem Elut column. When the liquid had been adsorbed the column was eluted with ethyl acetate and the eluate was concentrated by evaporation. The residue was purified on a silica gel Mega Bond Elut column, eluting with 5–40% ethyl acetate/hexane to give the title compound (0.085 g) as a glass. MS: 419 (M–H)$^-$.

Methods 27a–1

Using the procedure of Method 27 the following compounds were prepared.

| Meth | Replacement for 1-iodo-2-nitrobenzene | Replacement for (R)-N-(2-chloro-4-mercapto-phenyl)-2-hydroxy-2-methyl-3,3,3-trifluoropropanamide | Compound Prepared |
|---|---|---|---|
| 27a | (R)-N-[2-chloro-4-iodo-phenyl]-2-hydroxy-2-methyl-3,3,3-trifluoro-propanamide | 4-Nitrothiophenol | (R)-N-[2-chloro-4-(4-nitro-phenylthio)phenyl]-2-hydroxy-2-methyl-3,3,3-trifluoropropanamide |
| 27b | (R)-N-[2-chloro-4-iodo-phenyl]-2-hydroxy-2-methyl-3,3,3-trifluoro-propanamide | 2-Mercaptopyrimidine | (R)-N-[2-chloro-4-(pyrimidin-2-ylthio) phenyl]-2-hydroxy-2-methyl-3,3,3-trifluoro-propanamide |

| Meth | Replacement for 1-iodo-2-nitrobenzene | Replacement for (R)-N-(2-chloro-4-mercapto-phenyl)-2-hydroxy-2-methyl-3,3,3-trifluoropropanamide | Compound Prepared |
|---|---|---|---|
| 27c | (R)-N-[2-chloro-4-iodo-phenyl]-2-hydroxy-2-methyl-3,3,3-trifluoro-propanamide | 2-Mercaptothiazole | (R)-N-[2-chloro-4-(thiazol-2-ylthio)phenyl]-2-hydroxy-2-methyl-3,3,3-trifluoropropanamide |
| 27d | (R)-N-[2-chloro-4-iodo-phenyl]-2-hydroxy-2-methyl-3,3,3-trifluoro-propanamide | Sodium methanethiolate | (R)-N-(2-chloro-4-methylthiophenyl)-2-hydroxy-2-methyl-3,3,3-trifluoropropanamide |
| 27e | (R)-N-[2-chloro-4-iodo-phenyl]-2-hydroxy-2-methyl-3,3,3-trifluoro-propanamide | 2-Trifluoromethyl-thiophenol | (R)-N-[2-chloro-4-(2-trifluoromethylphenylthio)phenyl]-2-hydroxy-2-methyl-3,3,3-trifluoropropanamide |
| 27f | (R)-N-[2-chloro-4-iodo-phenyl]-2-hydroxy-2-methyl-3,3,3-trifluoro-propanamide | 4-Trifluoromethylthio-phenol | (R)-N-[2-chloro-4-(4-trifluoromethylphenylthio)phenyl]-2-hydroxy-2-methyl-3,3,3-trifluoropropanamide |
| 27g | (R)-N-[2-chloro-4-iodo-phenyl]-2-hydroxy-2-methyl-3,3,3-trifluoro-propanamide | 3-Trifluoromethylthio-phenol | (R)-N-[2-chloro-4-(3-trifluoromethylphenylthio)phenyl]-2-hydroxy-2-methyl-3,3,3-trifluoropropanamide |
| 27h[1] | 2-Iodo-5-methylthiophene | (R)-N-(2-chloro-4-mercapto-phenyl)-2-hydroxy-2-methyl-3,3,3-trifluoropropanamide | (R)-N-[2-chloro-4-(5-methyl-2-thienylthio)phenyl]-2-hydroxy-2-methyl-3,3,3-trifluoropropanamide |
| 27i | (R)-N-[2-chloro-4-iodo-phenyl]-2-hydroxy-2-methyl-3,3,3-trifluoro-propanamide | 2-Mercaptoimidazole | (R)-N-[2-chloro-4-(imidazol-2-ylthio)phenyl]-2-hydroxy-2-methyl-3,3,3-trifluoro-propanamide |
| 27j | (R)-N-[2-chloro-4-iodo-phenyl]-2-hydroxy-2-methyl-3,3,3-trifluoro-propanamide | 2-Mercaptopyridine | (R)-N-[2-chloro-4-(pyrid-2-ylthio)phenyl]-2-hydroxy-2-methyl-3,3,3-trifluoropropanamide |
| 27k | 3-Iodopyridine | (R)-N-(2-chloro-4-mercaptophenyl)-2-hydroxy-2-methyl-3,3,3-trifluoropropanamide | (R)-N-[2-chloro-4-(pyrid-3-ylthio)phenyl]-2-hydroxy-2-methyl-3,3,3-trifluoropropanamide |
| 27l | (R)-N-[2-chloro-4-iodo-phenyl]-2-hydroxy-2-methyl-3,3,3-trifluoro-propanamide | 3-mercapto-2-methylfuran | (R)-N-[2-chloro-4-((2-methylfuran-3-yl)thio)phenyl]-2-hydroxy-2-methyl-3,3,3-trifluoropropanamide |

[1]Product was purified by chromatography eluting with 25% ethyl acetate/hexane

Method 28

4-Phenylsulphonyl-2-fluorophenylethyne

Bis(triphenylphosphine)palladium(II) chloride (0.061 g) was added to a solution of ethynyltrimethylsilane (0.295 ml) and 2-fluoro-4-phenylsulphonylbromobenzene (Method 29) (0.548 g) in triethylamine (5.5 ml) and DMF (2 ml) and the mixture was heated at 70° C. for 18 hours. The mixture was poured into water (70 ml) and extracted with ethyl acetate (2×70 ml) to give a solid (0.46 g). A portion of this solid (0.30 g) was dissolved in dichloromethane (20 ml). Tetrabutylammonium fluoride (0.9 ml of a 1M solution in THF) was added. After 10 minutes volatile material was removed by evaporation and the residue was dissolved in dichloromethane and washed with brine. Chromatography of the crude product eluting with 0–30% ethyl. acetate/hexane gave the title compound (0.208 g) as a solid. NMR (CDCl$_3$): 3.42 (s, 1H), 7.5–7.7 (m, 6H), 7.94 (d, 2H); MS: 260 (M$^+$); EA: C$_{14}$H$_9$FO$_2$S requires C, 64.6; H, 3.5%; found: C, 64.6; H, 3.6%.

Method 29

2-Fluoro-4-phenylsulphonylbromobenzene

Using an analogous procedure to that described in Example 42, 4-bromo-3-fluoro-1-phenylthiobenzene (Method 19a) as the starting material and 20% ethyl acetate/hexane as the eluant for the chromatographic purification there was thus obtained the title compound. NMR (CDCl$_3$): 7.5–7.75 (m, 6H), 7.94 (d, 2H); EA: C$_{12}$H$_8$BrFO$_2$S requires C, 45.7; H, 2.6%; found: C, 46.1; H, 2.4%.

Method 30

(R)-N-[2-Chloro-4-(3-nitrophenylthio)phenyl]-2-hydroxy-2-methyl-3,3,3-trifluoropropanamide A mixture of 3-nitrophenyl disulphide (0.176 g) and (R)-N-(2-chloro-4-iodophenyl) 2-hydroxy-2-methyl-3,3,3-trifluoropropanamide (0.1 5 g) in diphenyl ether (5 ml) was heated and stirred at 250° C. for 2 days. The reaction mixture was cooled, diluted with isohexane (5 ml) and purified by chromatography eluting with 10–100% dichloromethane/hexane to give the title compound (0.05 g) as an oil. NMR (CDCl$_3$): 1.80 (s, 3H), 3.60 (s, 1H), 7.40–7.55 (m, 4H), 8.10 (br s, 2H), 8.45 (d, 1H), 9.05 (br s, 1H); MS: 421 (M+H)$^+$.

Method 31

(R)-N-(2-Chloro-4-mercaptophenyl)-2-hydroxy-2-methyl-3,3,3-trifluoropropanamide

Trifluoroacetic anhydride (5 ml) was added to (R)-N-(2-chloro-4-methylsulphinylphenyl)-2-hydroxy-2-methyl-3,3,3-trifluoropropanamide (Method 32)(0.188 g). The mixture was stirred and heated under reflux for 45 minutes then cooled and evaporated to dryness. A mixture of triethylamine (5 ml) and methanol (5 ml) was added to the residue. This mixture was stirred for a further 45 minutes then evaporated to dryness. The residue was dissolved in chloroform (50 ml), washed with saturated aqueous ammonium chloride solution (50 ml), dried and concentrated by evaporation to give the title compound (0.177 g) as a gum which was used without purification. MS 298 (M–H)$^-$.

Method 32

(R)-N-(2-Chloro-4-methylsulphinylphenyl)-2-hydroxy-2-methyl-3 3,3-trifluoropropanamide 1-Butylhydroperoxide (0.42 ml of a 5.5M solution in hexanes) was added to a solution of (R)-N-(2-chloro-4-methylthiophenyl)-2-hydroxy-2-methyl-3,3,3-trifluoropropanamide (Method 27d) (0.304 g) and camphorsulphonic acid (0.022 g) in chloroform (7 ml). The mixture was stirred for 18 hours and then was purified directly by chromatography eluting with 90% ethyl acetate/hexane to give the title compound (0.294 g) as a solid. NMR (CDCl$_3$): 1.77 (s, 3H), 2.74 (s, 3H), 4.7 and 4.75 (2xbr s, 1H), 7.49 (t, 1H), 7.74 (d, 1H), 8.59 (m, 1H), 9.3 (br d, 1H); MS: 328 (M–H)$^-$; EA: $C_{11}H_{11}ClF_3NO_3S.0.15\ Et_2O$ requires C, 40.9; H, 3.7; N, 4.1%; found: C, 40.7; H, 3.5; N, 3.9%.

Example 62

The following illustrate representative pharmaceutical dosage forms containing the compound of formula (I), or a pharmaceutically acceptable in vivo cleavable ester of said compound of formula (I) or a pharmaceutically acceptable salt of said compound or said ester (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium stearate | 1.5 |

| (e) Injection I | (50 mg/ml) |
|---|---|
| Compound X | 5.0% w/v |
| 1N Sodium hydroxide solution | 15.0% v/v |
| 0.1N Hydrochloric acid | (to adjust pH to 7.6) |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1N Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A method for producing an elevation of PDH activity in a warm-blooded animal in need of such treatment which comprises administering to said animal an effective amount of a compound of the formula (I):

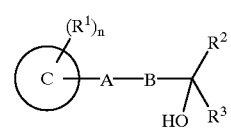

wherein:
    ring C is phenyl; wherein said phenyl is substituted at one or both positions meta to the position of A—B attachment or at the position para to the position of A—B attachment by a group selected from cyano, trifluoromethyl, nitro, trifluoromethoxy, trifluoromethylthio and a group ArY; and further, wherein said phenyl is substituted at any remaining meta position(s) or para position by a group or groups independently selected from hydrogen, (1–4C)alkyl, (1–4C)haloalkyl, (1–4C)alkoxy, (1–4C)haloalkoxy, (1–4C)alkenyloxy, cyano, nitro, halo, hydroxy and trifluoromethylthio; in which
    Ar is selected from the group consisting of phenyl, a carbon-linked six-membered heteroaryl ring containing 1–2 nitrogen atoms and a carbon-linked five-membered heteroaryl ring containing from 1–2 heteroatoms selected from nitrogen, oxygen, and sulphur; wherein said phenyl or heteroaryl ring Ar is optionally substituted at carbon, with 1–4 substituents selected from (1–4C)alkyl, (1–4C)haloalkyl, (1–4C)alkoxy, (1–4C) haloalkoxy, (2–4C)alkenyloxy, cyano, nitro, halo and trifluoromethylthio;
    Y is selected from carbonyl, sulphinyl and sulphonyl;
    A—B is selected from NHCO, OCH$_2$, SCH$_2$, NHCH$_2$, trans-vinylene, and ethynylene;
    R$^1$ is linked to ring C at a carbon ortho to the position of A—B attachment and is selected from the group consisting of (1–4C)alkyl, (1–4C)haloalkyl, (1–4C)alkoxy, (1–4C)haloalkoxy, (2–4C)alkenyloxy, cyano, nitro, halo, trifluoromethylthio and hydroxy;

n is 1 or 2;

$R^2$ and $R^3$ are independently (1–3C)alkyl optionally substituted by from 1 to 2k+1 atoms selected from fluoro and chloro wherein k is the number of carbon atoms in the said (1–3C)alkyl, provided that $R^2$ and $R^3$ are not both methyl; or $R^2$ and $R^3$, together with the carbon atom to which they are attached, form a 3–5 membered cycloalkyl ring optionally substituted by from 1 to 2m–2 fluorine atoms wherein m is the number of carbon atoms in said ring;

and a pharmaceutically acceptable in vivo cleavable ester of said compound of formula (I);

and a pharmaceutically acceptable salt of said compound or said ester; provided said compound is not N-(4-benzoyl-2,6-dimethylphenyl)-2-hydroxy-2-methyl-3,3,3-trifluoropropanamide, in the manufacture of a medicament for use in the elevation of PDH activity in warm-blooded animals such as humans.

2. The method as claimed in claim 1 wherein ring C is substituted at the position para to the position of A—B attachment by a group selected from cyano, trifluoromethyl, nitro, trifluoromethoxy and a group ArY wherein A—B and ArY are as defined in claim 1.

3. The method as claimed in claim 1 or 2 wherein Y is selected from sulphinyl and sulphonyl.

4. The method as claimed in claim 1 or 2 wherein A—B is NHCO.

5. The method as claimed in claim 1 or 2 wherein $R^1$ is selected from methoxy, nitro, fluoro, chloro, bromo and hydroxy and n is 1.

6. The method as claimed in claim 1 or 2 wherein one of $R^2$ and $R^3$ is methyl and the other is trifluoromethyl.

7. A compound of the formula (Ie):

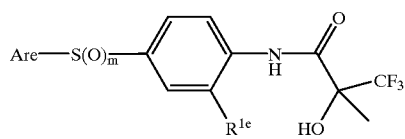

(Ie)

wherein:

$R^{1e}$ is fluoro, chloro or bromo;

m is 1 or 2;

Are is selected from the group consisting of a carbon-linked six-membered heteroaryl ring containing 1–2 nitrogen atoms and a carbon-linked five-membered heteroaryl ring containing from 1–2 heteroatoms selected from nitrogen, oxygen, and sulphur, wherein said heteroaryl ring is optionally substituted at carbon, with 1–4 substituents selected from (1–4C)alkyl, (1–4C)haloalkyl, (1–4C)alkoxy, (1–4C)haloalkoxy, (2–4C)alkenyloxy, cyano, nitro, halo and trifluoromethylthio;

and a pharmaceutically acceptable in vivo cleavable ester of said compound of formula (Ie), and a pharmaceutically acceptable salt of said compound or said ester.

8. A compound as claimed in claim 7 which is selected from:

(R)-N-[2-Chloro-4-(thien-2-yl-sulphonyl)phenyl]-2-hydroxy-2-methyl-3,3,3-trifluoropropanamide;

(R)-N-[2-Chloro-4-(pyrimid-2-yl-sulphonyl)phenyl]-2-hydroxy-2-methyl-3,3,3-trifluoropropanamide (R)-N-[2-Chloro-4-(pyrid-4-ylsulphonyl)phenyl]-2-hydroxy-2-methyl-3,3,3-trifluoropropanamide;

(R)-N-[2-(5-Methyl-thien-2-ylsulphonyl)phenyl]-2-hydroxy-2-methyl-3,3,3-trifluoropropanamide;

(R)-N-[2-Chloro-4-(imidazol-2-ylsulphonyl)phenyl]-2-hydroxy-2-methyl-3,3,3-trifluoropropanamide;

(R)-N-[2-Chloro-4-(pyrid-2-ylsulphonyl)phenyl]-2-hydroxy-2-methyl-3,3,3-trifluoropropanamide;

(R)-N-[2-Chloro-4-(pyrid-3-ylsulphonyl)phenyl]-2-hydroxy-2-methyl-3,3,3-trifluoropropanamide;

(R)-N-[2-Chloro-4-(thiazol-2-ylsulphonyl)phenyl]-2-hydroxy-2-methyl-3,3,3-trifluoropropanamide; and (R)-N-[2-Chloro-4-(2-methylfur-3-ylsulphonyl)phenyl]-2-hydroxy-2-methyl-3,3,3-trifluoropropanamide;

and a pharmaceutically acceptable in vivo cleavable ester of said compound;

and a pharmaceutically acceptable salt of said compound or said ester.

9. A pharmaceutical composition which comprises a compound of the formula (I) or (Ie) as defined in claim 7 or 8 or a pharmaceutically acceptable in vivo cleavable ester of said compound of formula (Ie) or a pharmaceutically acceptable salt of said compound or said ester, in association with a pharmaceutically acceptable excipient or carrier.

10. A process for preparing a compound of formula (Ie) as claimed in claim 7 or 8 which comprises:

(a) deprotecting a protected compound having formula (IIe):

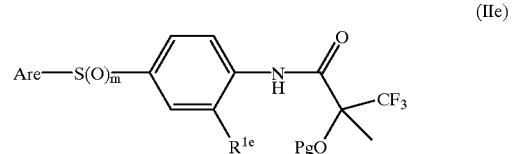

(IIe)

wherein "Pg" is a suitable alcohol protecting group;

(b) when $S(O)_m$ is sulphonyl: by treating a compound of formula (Ve):

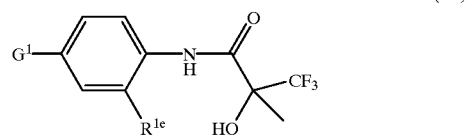

(Ve)

wherein $G^1$ is iodo, with a compound of formula $ArSO_2^-Na^+$ in the presence of a Cu(I) catalyst;

(c) by oxidizing a compound of formula (Ve) wherein $G^1$ is Are—S—;

(d) by coupling a compound of formula (VIe):

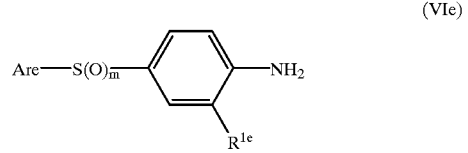

(VIe)

with an acid of formula (VIIe):

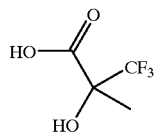
(VIIe)

(e) by coupling a compound of formula (VIe) with an activated acid derivative of an acid of formula (VIIe);

(f) by reacting an amide of formula (VIIIe):

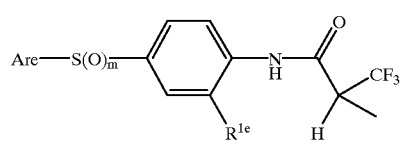
(VIIIe)

with a base and oxygen in the presence of a reducing agent;

(g) by reacting a compound of formula (IXe):

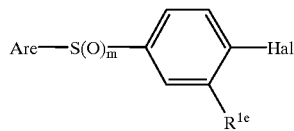
(IXe)

where Hal is halogen substituent, with an alkali metal amide dianion having formula (Xe):

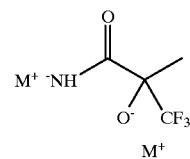
(Xe)

wherein M is an alkali metal;

(h) when $S(O)_m$ is sulphonyl: by treating a compound of formula (XIIe):

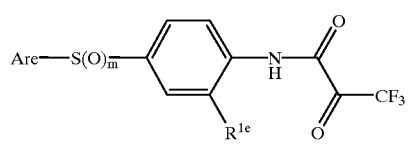
(XIIe)

with a compound of formula MeM wherein M is an alkali metal or a compound of formula MeMgBr or MeMgCl;

and thereafter if necessary:

i) converting a compound of the formula (Ie) into another compound of the formula (Ie);
ii) removing any protecting groups; or
iii) forming a pharmaceutically acceptable salt or in vivo cleavable ester.

\* \* \* \* \*